United States Patent
Rodríguez De Fonseca et al.

(10) Patent No.: US 11,058,650 B2
(45) Date of Patent: Jul. 13, 2021

(54) FATTY ACID AMIDES FOR THE PREVENTION AND/OR TREATMENT OF STEATOHEPATITIS

(71) Applicants: FUNDACIÓN RÚBLICA ANDALUZA PARA LA INVESTIGACIÓN DE MÁLAGA EN BIOMEDICINA Y SALUD (FIMABIS), Málaga (ES); CONSEJO SUPERIOR DE INVESTIGACIONES CIENTÍFICAS, Madrid (ES); FUNDACIÓ INSTITUT MAR D'INVESTIGACIONS MÉDIQUES, Barcelona (ES)

(72) Inventors: Fernando Rodríguez De Fonseca, Málaga (ES); Francisco Javier Pavón Morón, Málaga (ES); Juan Manuel Decara Del Olmo, Málaga (ES); Antonia Serrano Criado, Málaga (ES); Jesús Joglar Tamargo, Madrid (ES); Pedro Clapés Saborit, Madrid (ES); Rafael De La Torre Fornell, Barcelona (ES); Magí Ferre Albaladejo, Barcelona (ES); María Isabel Covas Planells, Barcelona (ES); Montserrat Fito Colomer, Barcelona (ES); Bruno Almeida Cotrim, Barcelona (ES)

(73) Assignees: FUNDACIÓN PÚBLICA ANDALUZA PARA LA INVESTIGACIÓN DE MÁLAGA EN BIOMEDICINA Y SALUD (FIMABIS), Malaga (ES); CONSEJO SUPERIOR DE INVESTIGACIONES CIENTÍFICAS (CSIC), Madrid (ES); FUNDACIÓ INSTITUT MAR DTNVESTIGACIONS MÈDIOUES, Barcelona (ES)

(*) Notice: Subject to any disclaimer, the term of this patent is extended or adjusted under 35 U.S.C. 154(b) by 0 days.

(21) Appl. No.: 15/529,433

(22) PCT Filed: Nov. 24, 2015

(86) PCT No.: PCT/ES2015/070848
§ 371 (c)(1),
(2) Date: Oct. 9, 2017

(87) PCT Pub. No.: WO2016/083646
PCT Pub. Date: Jun. 2, 2016

(65) Prior Publication Data
US 2018/0193293 A1    Jul. 12, 2018

(30) Foreign Application Priority Data

Nov. 24, 2014 (ES) .................. ES201431739

(51) Int. Cl.
A61K 31/165 (2006.01)
A61P 1/16 (2006.01)

(52) U.S. Cl.
CPC .............. *A61K 31/165* (2013.01); *A61P 1/16* (2018.01)

(58) Field of Classification Search
USPC ........................................................ 514/627
See application file for complete search history.

(56) References Cited

FOREIGN PATENT DOCUMENTS

WO    WO 2011/076966    *    6/2011

OTHER PUBLICATIONS

Luyckx et al. Non-alcoholic steatohepatitis: association with obesity and insulin resistance, and influence of weight loss. (Diabetes & Metabolism, 2000, 26, 98-106).*
Garcia-Monzon et al. Characterization of pathogenic and prognostic factors of nonalcoholic steatohepatitis associated with obesity. Journal of Hepatology, 2000, 33, 716-724.*
Almeida et al. Synthesis of fatty acid amides of catechol metabolites that exhibit antiobesity properties. ChemMedChem 2010, 5, 1781-1787.*
De la Torre et al. Machine translation of WO 2011/076966. Translation made Dec. 2018.*
Carr et al., "Endocannabinoids, metabolic regulation, and the role of diet," *Nutrition Research* 28:641-650, 2008.
Easl et al., "EASL-EASD-EASO Clinical Practice Guidelines for the management of nonalcoholic fatty liver disease," *Journal of Hepatology* 64:1388-1402, 2016.
Gaudette et al., "Did Statins Reduce the Health and Health Care Costs of Obesity?" *Pharmacoeconomics*. 33(7):723-734, 2015.
Golub et al., "Greasing the Wheels of Managing Overweight and Obesity with Omega-3 Fatty Acids," *Med Hypotheses* 77(6): 1114-1120, 2011.
Leoni et al., "Current guidelines for the management of non-alcoholic fatty liver disease: A systematic review with comparative analysis," *World J Gastroenterol* 24(30):3361-3373, 2018.
Levri et al., "Metformin as Treatment for Overweight and Obese Adults: A Systematic Review," *Ann Fam Med* 3(5): 457-461, 2005.
Pillarisetti et al., "Pain and beyond: fatty acid amides and fatty acid amide hydrolase inhibitors in cardiovascular and metabolic diseases," *Drug Discovery Today* 14(23-24):1098-1111, 2009.
Wang et al., "N-3 Polyunsaturated Fatty Acids and Inflammation in Obesity: Local Effect and Systemic Benefit," *BioMed Research International* 2015:1-16, 2015.

(Continued)

Primary Examiner — Kathrien A Cruz
(74) Attorney, Agent, or Firm — Seed IP Law Group LLP

(57) ABSTRACT

The invention relates to the use of fatty acid amides with phenylalkylamines and of a pharmaceutical composition comprising at least one of these compounds in the prevention and/or treatment of fatty liver or a pathological condition or disease caused by fatty liver, either alcoholic or non-alcoholic, and, in particular, for the prevention and/or treatment of the alcoholic steatohepatitis or non-alcoholic steatohepatitis (NASH).

14 Claims, 19 Drawing Sheets

(56) References Cited

OTHER PUBLICATIONS

Pavón et al., "Oleoylethanolamide: a new player in peripheral control of energy metabolism. Therapeutic implications," *Drug Discovery Today: Disease Mechanisms* 7(3-4):175-183, 2010.
Abdelmalek et al., "Increased Fructose Consumption Is Associated with Fibrosis Severity in Patients with Nonalcoholic Fatty Liver Disease," *Hepatology* 51(6):1961-1971, 2010.
Chalasani et al., "The Diagnosis and Management of Nonalcoholic Fatty Liver Disease: Practice Guidance From the American Association for the Study of Liver Diseases," *Hepatology* 67(1):328-357, 2018.
Cortez-Pinto et al., "Alterations in Liver ATP Homeostasis in Human Nonalcoholic Steatohepatitis: A Pilot Study," *JAMA* 282(17):1659-1664, 1999.
D'Albuquerque et al., "Liver Transplantation for Subacute Hepatocellular Failure due to Massive Steatohepatitis After Bariatric Surgery," *Liver Transplantation* 14:881-885, 2008.
Leoni et al., "Current guidelines for the management of non-alcoholic fatty liver disease: A systematic review with comparative analysis," *World Journal of Gastroenterology* 24(30):3361-3373, 2018. (18 pages).
Marí et al., "Mechanism of Mitochondrial Glutathione-Dependent Hepatocellular Susceptibility to TNF Despite NF-κB Activation," *Gastroenterology* 134:1507-1520, 2008.
Marí et al., "Mitochondrial free cholesterol loading sensitizes to TNF- and Fas-mediated steatohepatitis," *Cell Metabolism* 4:185-198, 2006.
Musso et al., "Adiponectin Gene Polymorphisms Modulate Acute Adiponectin Response to Dietary Fat: Possible Pathogenetic Role in NASH," *Hepatology* 47(4):1167-1177, 2008.
Polotsky et al., "Obstructive Sleep Apnea, Insulin Resistance, and Steatohepatitis in Severe Obesity," *Am J Respir Crit Care Med* 179:228-234, 2009.
Rich et al., "Racial and Ethnic Disparities in Nonalcoholic Fatty Liver Disease Prevalence, Severity, and Outcomes in the United States: A Systematic Review and Meta-analysis," *Clinical Gastroenterology and Hepatology* 16:198-210, 2018.
Younossi et al., "Global burden of NAFLD and NASH: trends, predictions, risk factors, and prevention," *Nature Reviews Gastroenterology & Hepatology* 15:11-20, 2018.
Zelman, "The Liver in Obesity," *AMA Arch Intern Med* 90(2):141-156, 1952.
Alen et al., "PPARα/CB1 receptor dual ligands as a novel therapy for alcohol use disorder: Evaluation of a novel oleic acid conjugate in preclinical rat models," *Biochemical Pharmacology* 157:235-243, 2018.
"Novel conjugation of oleic acid with an amphetamine derivate for prevention and treatment of steatohepatitis," biospain 2018, Sep. 26, 2018, 33 pages.
Decara et al., "Treatment with a novel oleic-acid-dihydroxyamphetamine conjugation ameliorates non-alcoholic fatty liver disease in obese Zucker rats," *Disease Models & Mechanisms* 8:1213-1225, 2015.

* cited by examiner

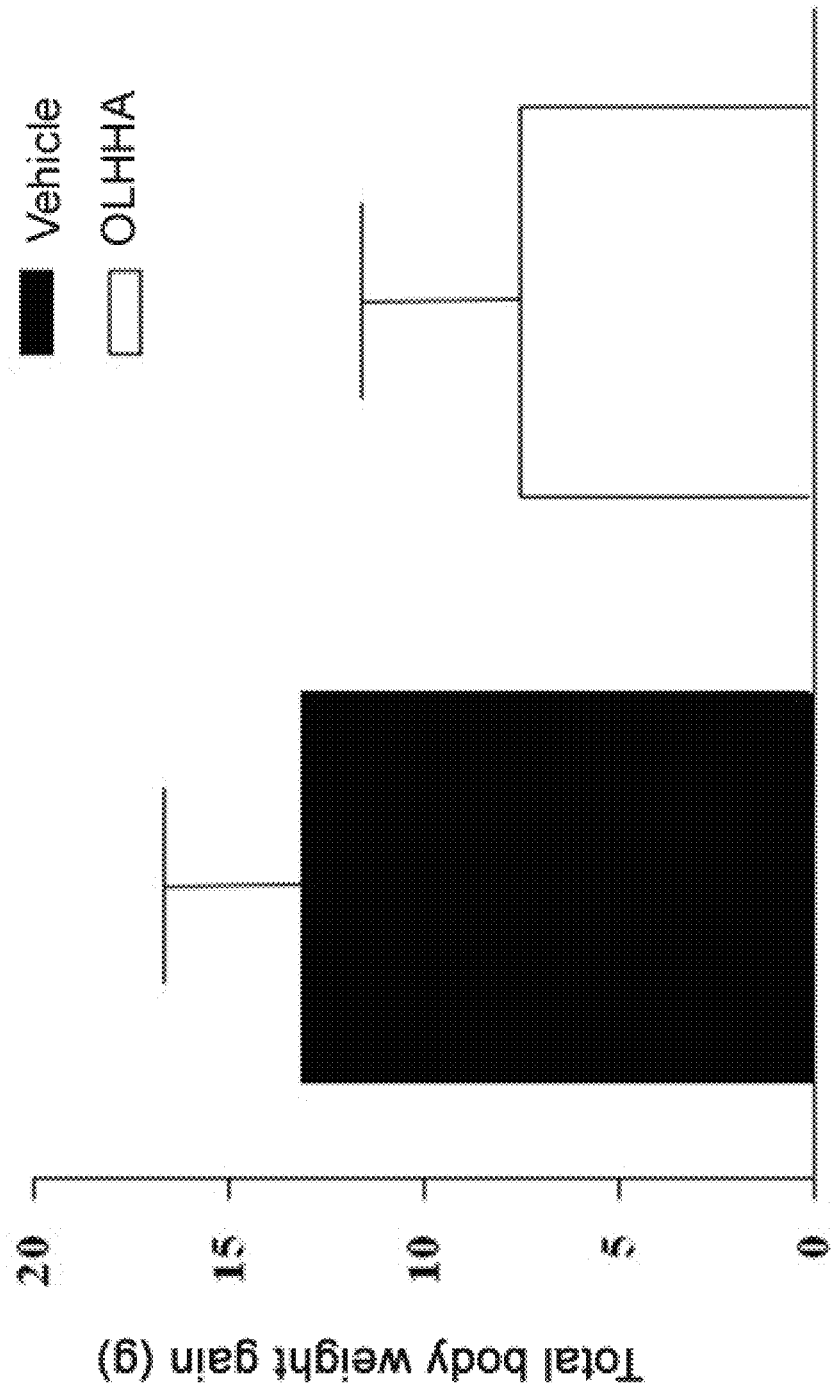

Fig.8

| Standard control inhibitors | IC50 µM |
|---|---|
| Amiodarone | 1.7 ± 0.2 |
| Bepridil | 2.2 ± 0.3 |
| Haloperidol | 1.9 ± 0.1 |
| Terfenadine | 1.0 ± 0.3 |
| OLHHA | > 150 |

Figura 9
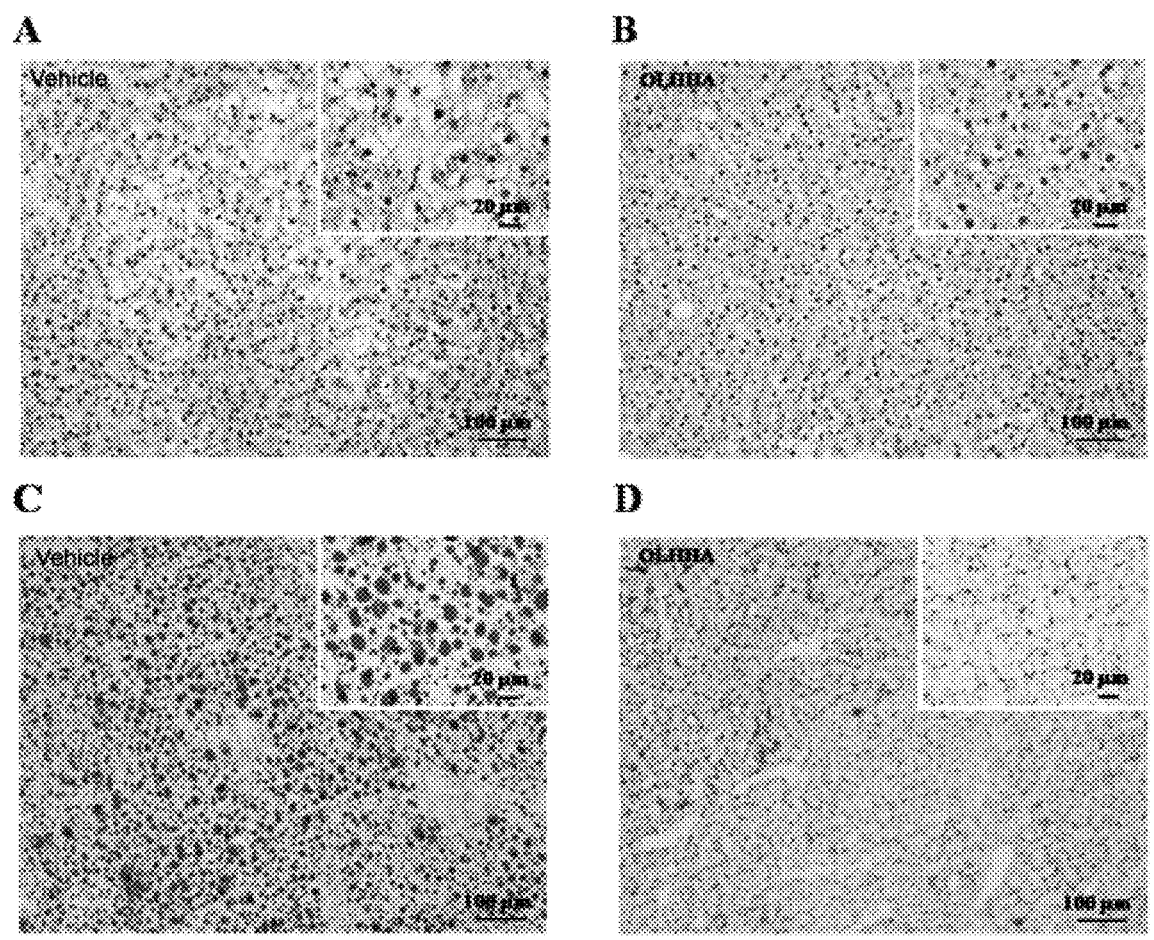

Figura 10
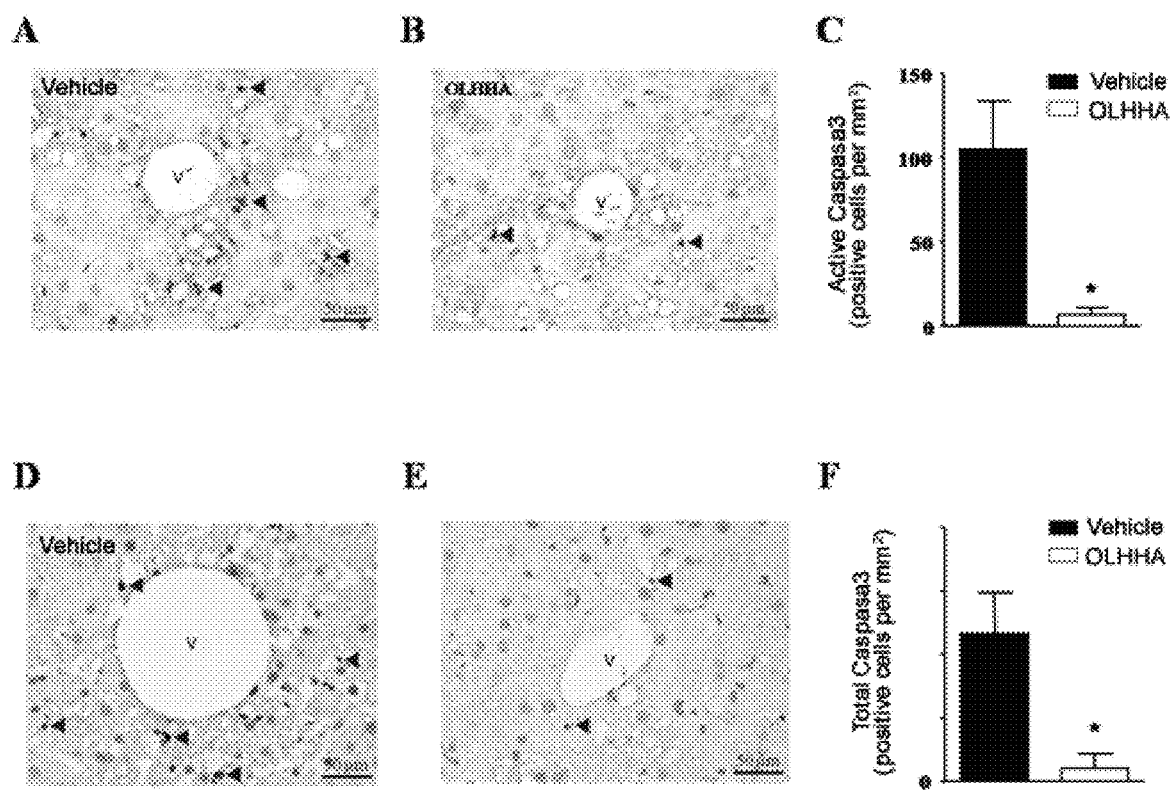

Figura 11
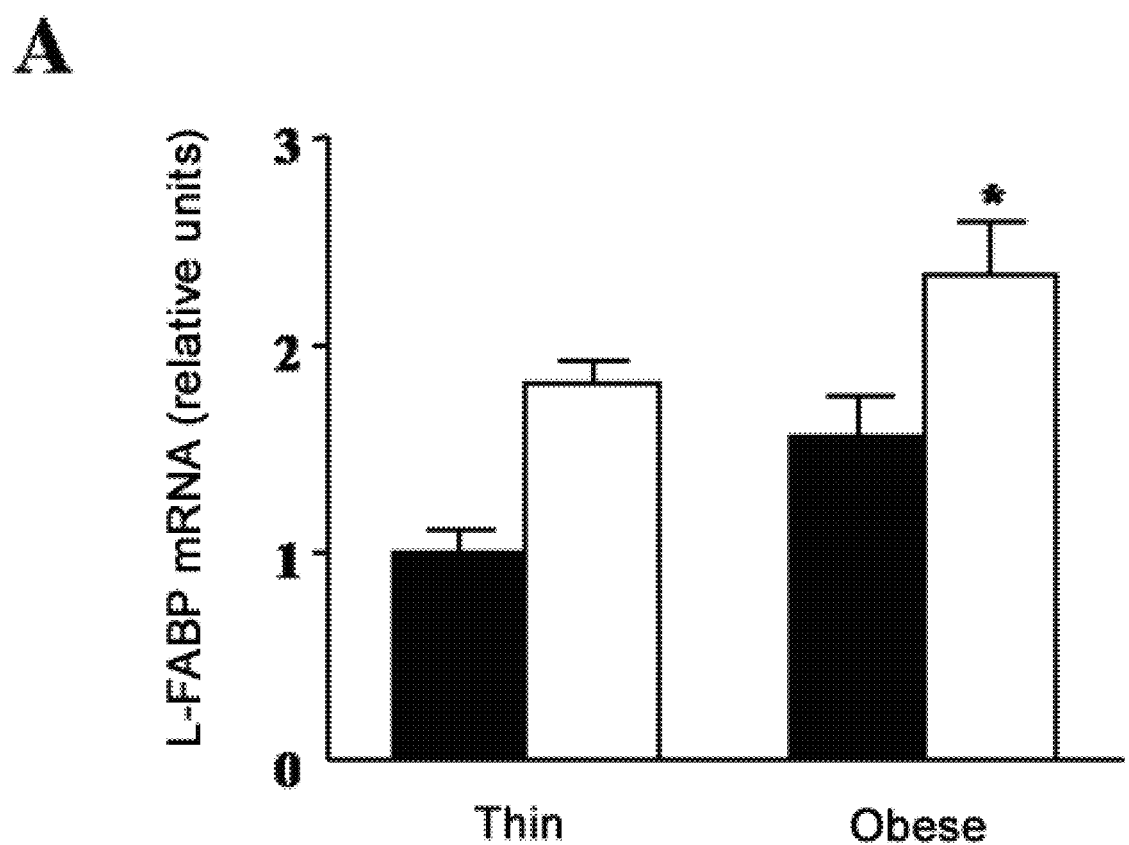

Figura 12
A
Obese Zucker rats
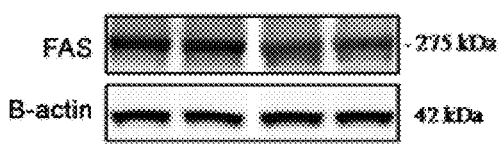
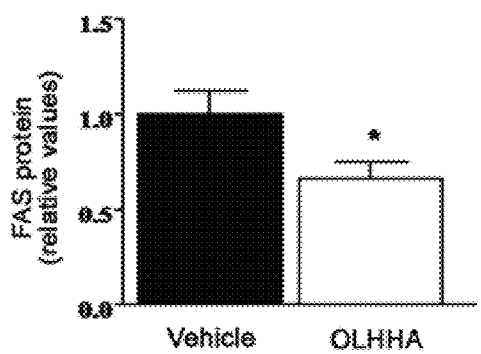
B
Obese Zucker rats
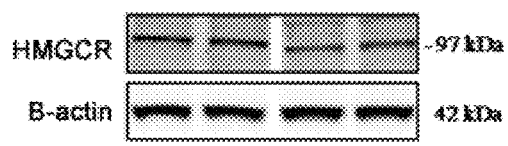
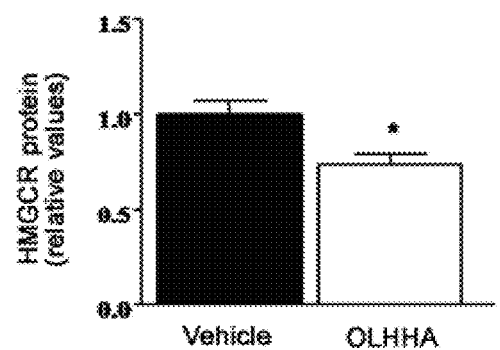
C
Obese Zucker rats
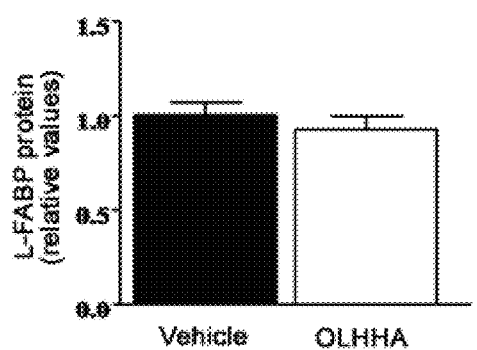
D
Obese Zucker rats
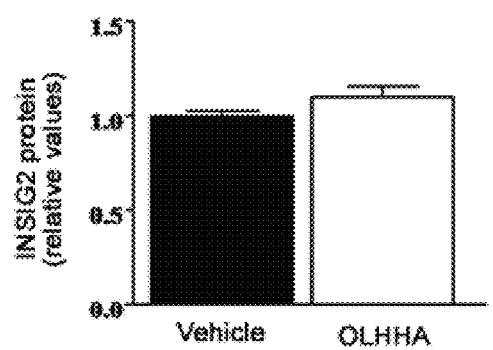

FATTY ACID AMIDES FOR THE PREVENTION AND/OR TREATMENT OF STEATOHEPATITIS

FIELD OF THE INVENTION

The present invention is comprised in the field of medicine and pharmacy, and relates to a new series of fatty acid amides with phenylalkylamines and the pharmaceutically acceptable salts, solvates and hydrates thereof, and more specifically, it relates to the use of the compound N-(1-(3, 4-dihydroxyphenyl)propan-2-yl)oleamide (OLHHA) for preparing a medicinal product for the prevention and/or treatment of fatty liver disease, preferably non-alcoholic fatty liver disease (NAFLD) and, particularly, for preparing a medicinal product for the prevention and/or treatment of steatohepatitis, preferably non-alcoholic steatohepatitis (NASH). The treatment allows reducing the liver fat mass, which leads to an improvement in patient health.

BACKGROUND OF THE INVENTION

Steatohepatitis is a liver disease caused by lipid accumulation in hepatocytes and it is one of the main causes of liver-related morbidity worldwide. Generally, steatohepatitis is etiologically differentiated into two groups depending on the presence of the only known main factor triggering it: abusive alcohol consumption. In this sense, steatohepatitis is differentiated into alcoholic steatohepatitis and non-alcoholic steatohepatitis (NASH). NASH is a common liver disease. It is often "silent", i.e., it has no symptoms. NASH is similar to liver diseases caused by alcohol consumption, but occurs in people who drink little or no alcohol.

The main characteristic of NASH is fat in the liver with inflammation and damage. Most people suffering from NASH feel fine. They do not know that they have a liver problem. NASH can be serious and lead to cirrhosis. With cirrhosis, the liver is permanently damaged, forms scars and stops working correctly.

NASH affects between 2 and 5% of the people living in the United States. Other percentage, from 10 to 20%, of people has fat in the liver without having liver inflammation or damage. This medical condition is called "fatty liver". It is not normal to have fat in the liver. However, having fat in the liver alone is not likely to cause a lot of damage or permanent damage. The presence of fat can be observed with a blood test, a liver ultrasound (sonography) or a similar test. If the results of the blood test, the sonography or other tests show the possibility of there being fat in the liver, the disease is called "non-alcoholic fatty liver disease" (NAFLD). A liver biopsy will detect if one has NASH or NAFLD.

NASH is becoming increasingly common. This can be due to the higher prevalence of obesity among people living in the United States. In the last 10 years, the number of adults who have become obese has doubled and the number of children tripled. Obesity also leads to diabetes and a high blood cholesterol level, which can wreak havoc to the health of someone with NASH. In Spain, the figures show prevalence exceeding 20%, being particularly prevalent in men, in whom it is associated with metabolic syndrome, and in obese children. In children, this prevalence is on the rise due to the growing epidemic of childhood overweight (Gelpi Méndez et al., 2014. Arch. Prev. Riesgos Labor. 17(2), 84-90; Navarro-Jarabo et al., 2013. *J. Gastroenterol. Hepatol.* 28(9):1532-8; Caballeria et al., 2012. *Eur. J. Gastroenterol. Hepatol.* 24(9):1007-11).

There is currently no treatment specific for NASH. The most important recommendations for people suffering from this disease are for them to:
1. reduce weight (if they are obese or overweight).
2. eat a balanced and healthy diet.
3. do more physical activity.
4. avoid alcohol consumption.
5. avoid taking unnecessary medicines.

Following these recommendations will help preventing early liver damage or reversing it in the earliest stages. They are also useful for other medical conditions, such as heart diseases, diabetes and high cholesterol. People must make a huge effort to maintain a healthy body weight. Weight loss can improve the results of liver tests in people with NASH. Reducing weight can even reverse the disease to some extent. Researchers are trying to find out how many kilograms a person with NASH must lose in order to improve the liver. They also wish to know if reducing weight has any long-term effects.

People with NASH often suffer from other diseases, such as diabetes, high blood pressure or dyslipidemia (higher-than-normal triglyceride and/or cholesterol levels). These medical conditions must be treated with medicines and suitably controlled. The people must not stop treating other conditions simply because they suffer from NASH or have high liver enzyme levels.

There are two experimental treatments for people with NASH:
  a) Antioxidants, such as vitamin E, selenium and betaine:
      It is not known whether these substances help to treat the disease, but the results of the studies will be available in the upcoming years.
  b) New medicinal products for the treatment of diabetes: these products are even used in people without diabetes. This is due to the fact that most people with NASH have insulin resistance. This means that the insulin normally present in blood does not control glucose and fatty acids efficiently. These new medicinal products improve the body's sensitivity to insulin.

It is therefore necessary to develop a treatment specific for NASH.

BRIEF DESCRIPTION OF THE INVENTION

A first aspect of the present invention relates to the use of a compound of general formula (I) (also referred to as the compound of the invention):

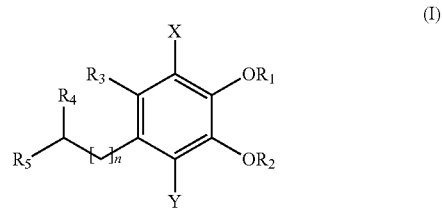

where
X and Y can independently be the same or different and are selected from H, halogen and methyl;
n is an integer from 1 to 4;
$R_1$ and $R_2$ can independently be the same or different and are selected from H and $C_1$-$C_6$ alkyl or can be bound by a single bond between the two oxygen atoms, forming a new ring;

$R_3$ is selected from H, $C_1$-$C_6$ alkyl and $C_1$-$C_4$ alkenyl;
$R_4$ is selected from H, halogen and $C_1$-$C_4$ alkyl;
$R_5$ is a compound of general formula (II):

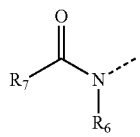

(II)

where:
$R_6$ is selected from H and $C_1$-$C_4$ alkyl;
$R_7$ is selected from $C_8$-$C_{30}$ alkyl and $C_8$-$C_{30}$ alkenyl;
or any of the salts thereof, preferably any pharmaceutically acceptable salt, pharmaceutically acceptable esters, tautomers, polymorphs, hydrates, or an isomer, prodrugs, derivatives, solvates or analogues, or any of the combinations thereof, in the preparation of a medicinal product for the prevention, relief and/or treatment of fatty liver or a pathological condition or disease caused by fatty liver. Alternatively, it relates to the compound of the invention or any of the salts thereof, preferably any pharmaceutically acceptable salt, pharmaceutically acceptable esters, tautomers, polymorphs, hydrates, or an isomer, prodrugs, derivatives, solvates or analogues, or any of the combinations thereof, for use in the prevention, relief and/or treatment of fatty liver or a pathological condition or disease caused by fatty liver.

In a preferred embodiment of this aspect of the invention, the disease caused by fatty liver is steatohepatitis.

In a preferred embodiment of this aspect of the invention, the compound is used in the preparation of a medicinal product for the prevention, relief and/or treatment of a disease caused by non-alcoholic fatty liver disease (NAFLD), more preferably non-alcoholic steatohepatitis (NASH).

In a preferred embodiment of this aspect of the invention, X and Y can independently be the same or different and are selected from H and $CH_3$.

In a preferred embodiment of this aspect of the invention, n is an integer selected from 1 or 3, more preferably 1.

In another preferred embodiment of this aspect of the invention, $R_1$ and $R_2$ can independently be the same or different and are selected from H and $CH_3$ or can be bound by a single bond between the two oxygen atoms, forming a new ring.

In another preferred embodiment of this aspect of the invention, $R_3$ is selected from H and $C_1$-$C_3$ alkyl, and is more preferably H.

In another preferred embodiment of this aspect of the invention, $R_4$ is selected from H and $CH_3$, and is more preferably $CH_3$.

In another preferred embodiment of this aspect of the invention, $R_5$ is a compound of formula (II):

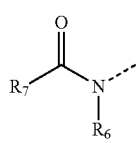

(II)

where $R_6$ is selected from H and $CH_3$ and $R_7$ is a $C_{15}$-$C_{25}$ alkenyl group.

In another preferred embodiment of this aspect of the invention, $R_7$ has a number of unsaturations between 1 and 6, more preferably between 1 and 4.

In another preferred embodiment of the invention, the compound of general formula (I) relates to a compound which is selected from the following group:

Formula (III)

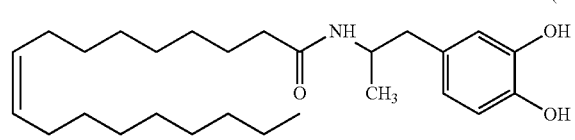

Formula (IV)

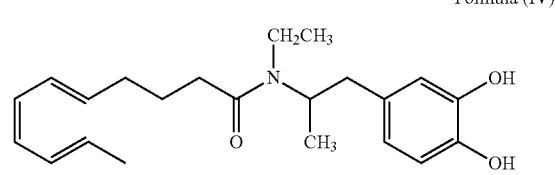

Formula (V)

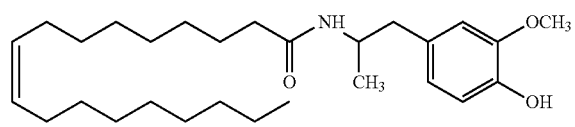

Formula (VI)

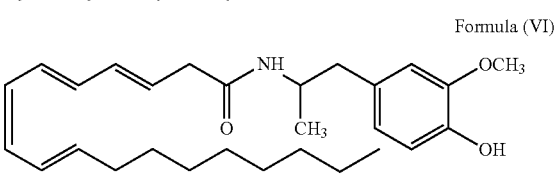

Formula (VII)

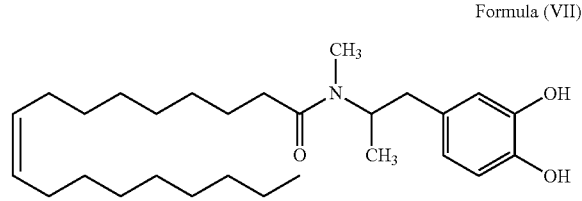

Formula (VIII)

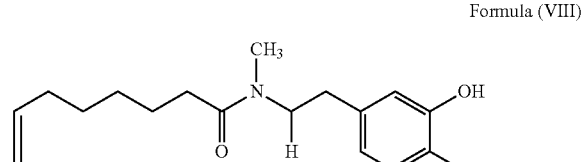

Formula (IX)

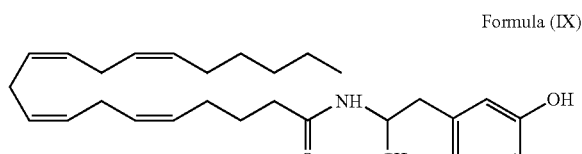

Formula (X)

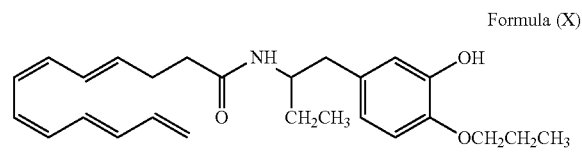

-continued

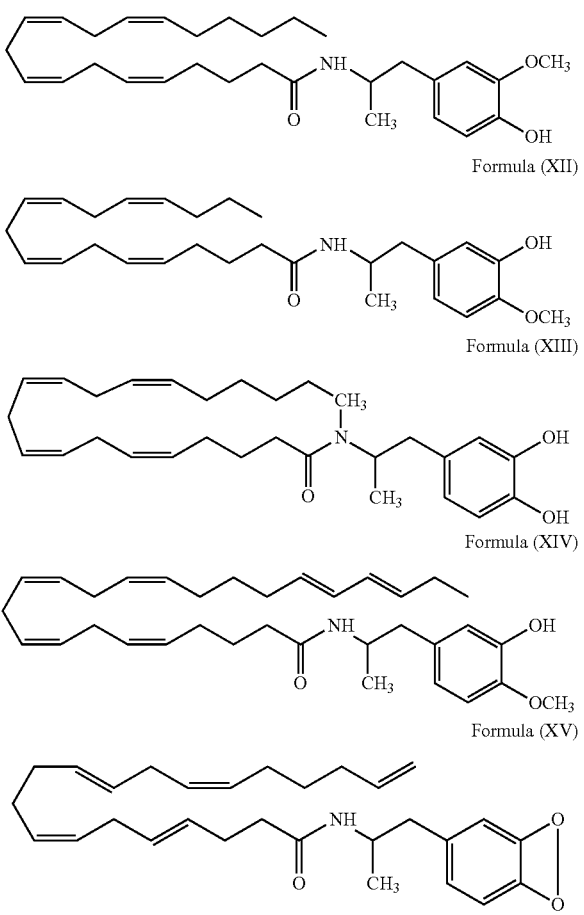

or any of the salts thereof, preferably a pharmaceutically acceptable salt, pharmaceutically acceptable esters, tautomers, polymorphs, hydrates, or an isomer, prodrugs, derivatives, solvates or analogues, or any of the combinations thereof, or any of the combinations thereof.

In a preferred embodiment of this aspect of the invention, the compound is N-(1-(3,4-dihydroxyphenyl)propan-2-yl) oleamide (OLHHA).

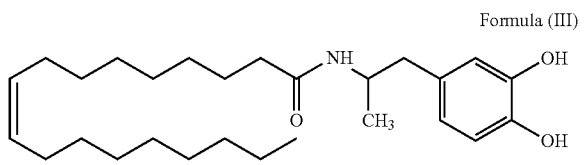 [SMILES: CCCCCCCC/C=C\CCCCCCCC(=O)NC(C)Cc1ccc(O)c(O)c1]

A second aspect of the invention relates to the use of a pharmaceutical composition comprising at least one compound of the invention, or a tautomer, a pharmaceutically acceptable salt, a derivative or a prodrug thereof, in the preparation of a medicinal product for the prevention, relief and/or treatment of a disease caused by fatty liver. Alternatively, it relates to a pharmaceutical composition comprising at least one compound of the invention or any of the salts, preferably any pharmaceutically acceptable salt, pharmaceutically acceptable esters, tautomers, polymorphs, hydrates, or an isomer, prodrugs, derivatives, solvates or analogues, or any of the combinations thereof, for use in the prevention, relief and/or treatment of a disease caused by fatty liver. In a preferred embodiment of this aspect, the composition of the invention further comprises a pharmaceutically acceptable carrier, a pharmaceutically acceptable excipient and/or a vehicle.

In a preferred embodiment of this aspect of the invention, the disease caused by fatty liver is steatohepatitis.

In another preferred embodiment of this aspect of the invention, the pharmaceutical composition of the invention is used in the preparation of a medicinal product for the prevention, relief and/or treatment of a disease caused by non-alcoholic fatty liver disease (NAFLD), preferably non-alcoholic steatohepatitis (NASH).

In another preferred embodiment of this aspect of the invention, the pharmaceutical composition of the invention is used for the prevention, relief or treatment of a disease caused by alcoholic fatty liver disease (AFLD), preferably alcoholic steatohepatitis (ASH).

In another preferred embodiment, the pharmaceutical composition further comprises another active ingredient.

A third aspect of the invention relates to a food composition or a nutraceutical composition or a medical food-type composition, hereinafter food composition of the invention, comprising at least one of the compounds of formula (I).

A fourth aspect of the invention relates to the use of the food composition of the invention for the prevention, relief or treatment of fatty liver or a pathological condition or disease caused by fatty liver, preferably steatohepatitis in mammals, and more preferably in human beings. Alternatively, it relates to the use of the food composition of the invention for the prevention and/or treatment of fatty liver or a pathological condition or disease caused by fatty liver, preferably steatohepatitis.

In a preferred embodiment of this aspect of the invention, the food composition of the invention is used for the prevention, relief or treatment of a disease caused by non-alcoholic fatty liver disease (NAFLD), preferably non-alcoholic steatohepatitis (NASH).

In another preferred embodiment of this aspect of the invention, the food composition of the invention is used for the prevention, relief or treatment of a disease caused by alcoholic fatty liver disease (AFLD), preferably alcoholic steatohepatitis (ASH).

Another aspect of the invention relates to a method for the prevention, relief or treatment of a subject, preferably a human being, suffering from a disease caused by alcoholic fatty liver disease (AFLD), preferably alcoholic steatohepatitis (ASH), or a disease caused by non-alcoholic fatty liver disease (NAFLD), preferably non-alcoholic steatohepatitis (NASH), which comprises administering the food composition of the invention or the pharmaceutical composition of the invention.

DESCRIPTION OF THE DRAWINGS

FIG. 9 shows the histological evaluation of the effect of chronic treatment with OLHHA on fatty liver in obese Zucker rats. (A, B) Hematoxylin-eosin; (C, D) Oil red.

FIG. 10 shows the effect of chronic treatment with OLHHA on the expression of Caspasa-3 in the liver of obese Zucker rats. (A, B, C) Immunohistochemistry and quantification of cells positive for activated Caspasa-3; (D, E, F) Immunohistochemistry and quantification of cells positive for total Caspasa-3.

FIG. 11 shows the effect of chronic treatment with OLHHA on the gene expression of the L-FABP protein in the liver of Zucker rats (A).

FIG. 12 shows the effect of chronic treatment with OLHHA on the protein levels of the enzymes involved in lipid metabolism in the liver of obese Zucker rats. (A) FAS; (B) HMG-CoAR; (C) L-FABP; (D) INSIG2.

DETAILED DESCRIPTION OF THE INVENTION

Figure 1:
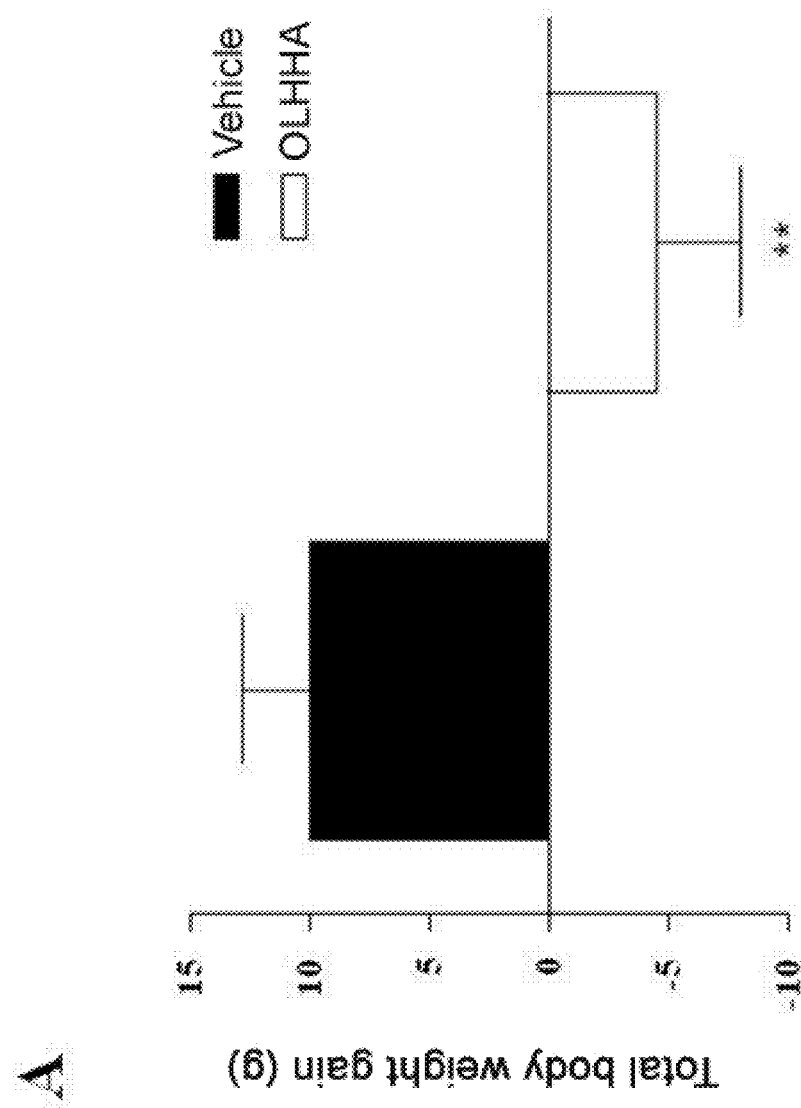
FIG. 1 shows the effects of chronic treatment with OLHHA on body weight gain and intake in Zucker rats.
Figure 1:
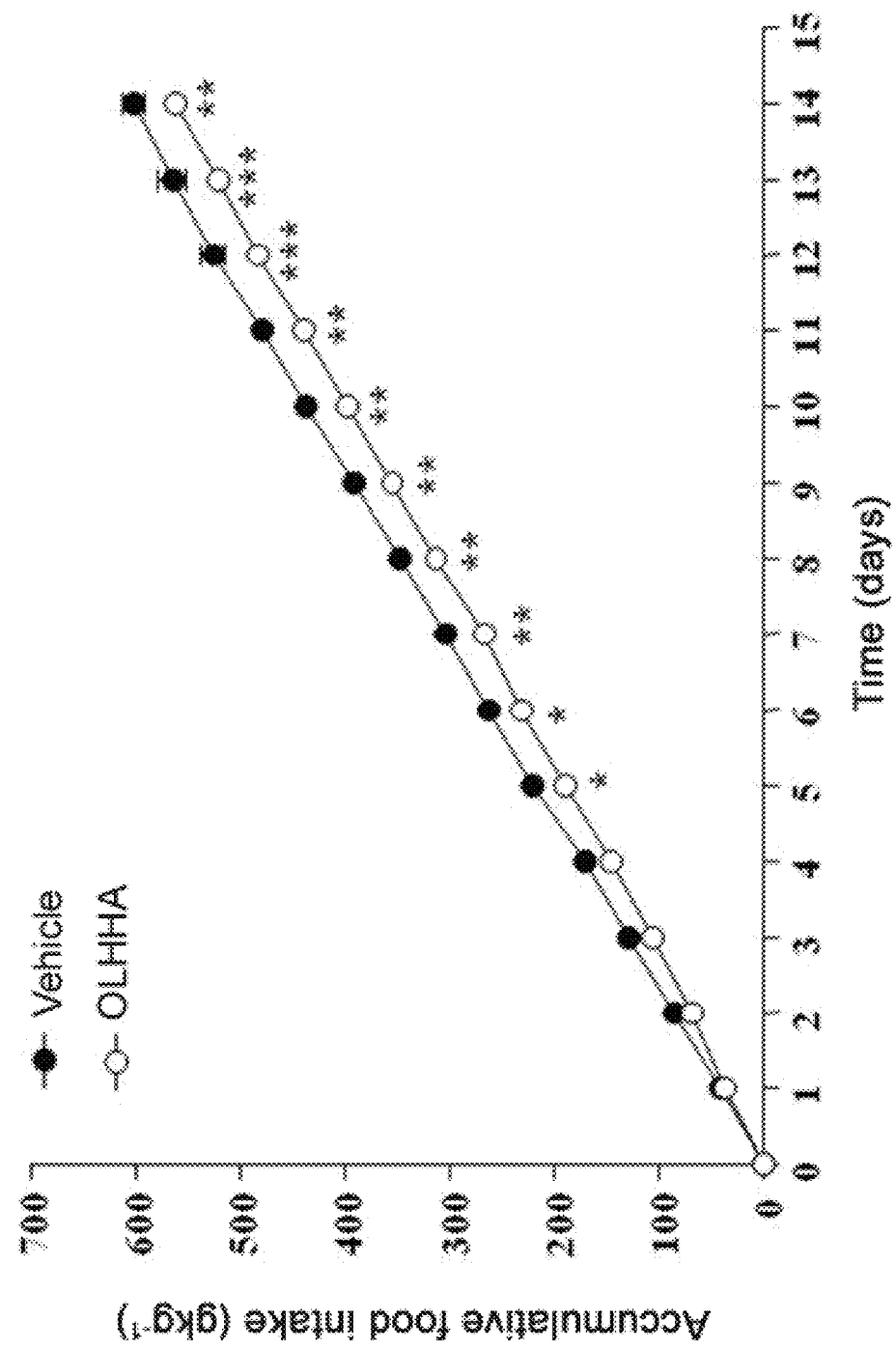
Figure 1:
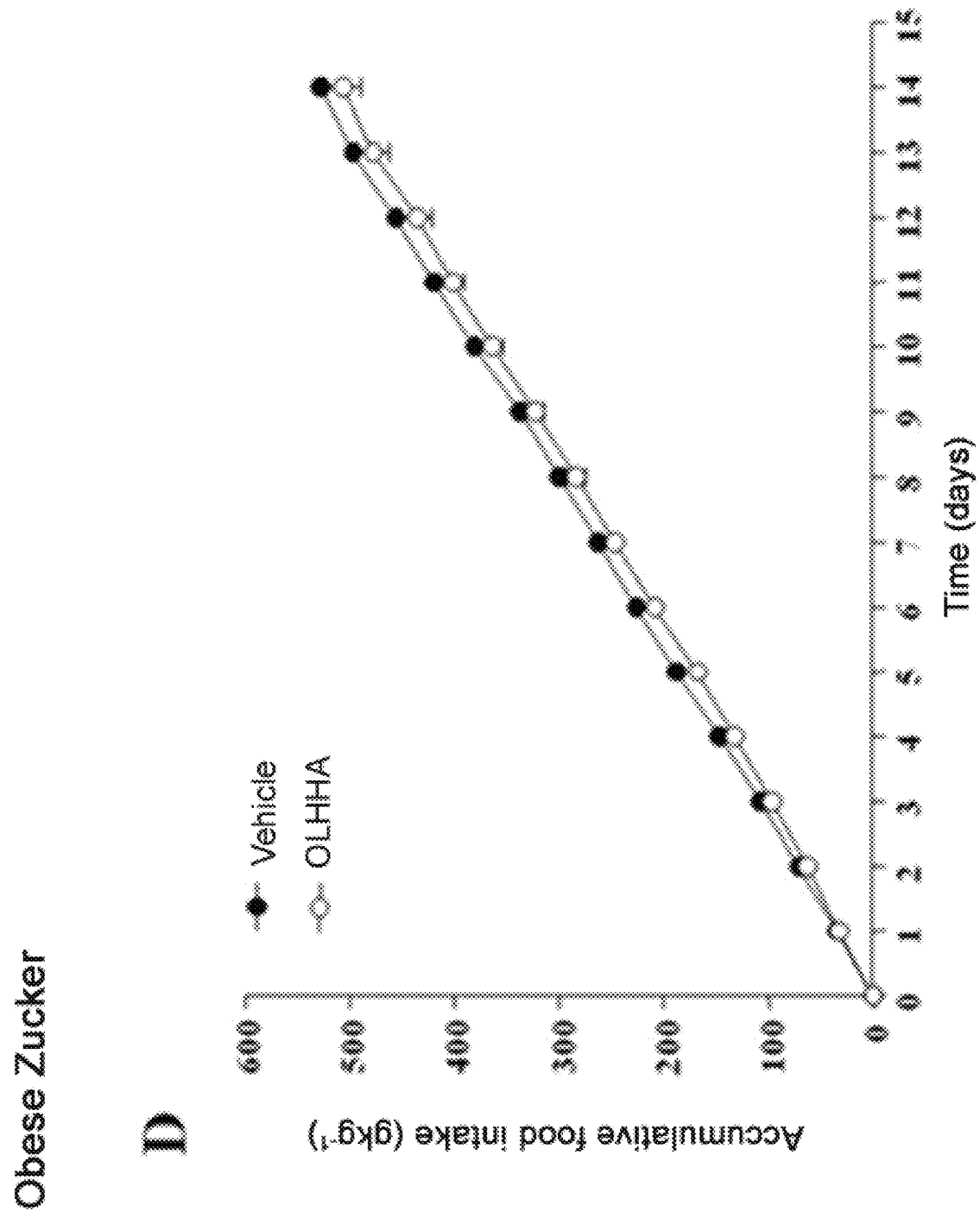

The results presented in the invention show that the compound: N-(1-(3,4-dihydroxyphenyl)propan-2-yl)oleamide (OLHHA), mitigates fatty liver in a genetic model of obesity such as Zucker rats, which suggests the liver protective role of this compound. Obese Zucker rats showed high serum triglyceride levels and fatty liver, which is confirmed as a significant increase in circulating triglycerides and the total liver fat content in comparison with the thin animals. With the administration of the compound of the present invention, both the serum triglyceride level and the lipid accumulation level were reduced in the liver of obese Zucker rats treated with OLHHA. This effect has been associated with changes in the mRNA gene expression related with lipid metabolism in the liver. In other words, OLHHA reduced the gene expression of lipogenic enzymes, including fatty acid synthase (FAS) and 3-hydroxy-3-methyl-glutaryl-CoA reductase (HMG-CoAR) and increased the gene expression of enzymes which promote fatty acid oxidation, such as acyl-CoA oxidase (ACOX). The drop in the HMG-CoAR mRNA level was related with an increase in the gene expression of insulin-induced gene 2 (INSIG2), which is involved in cholesterol biosynthesis regulation. Finally, OLHHA caused a reduced gene expression of the N-acyl phosphatidylethanolamine phospholipase D (NAPE-PLD) endocannabinoid system-related pro-lipogenic enzyme. OLHHA also showed a safe pharmacological profile because it does not interact with the human ether-à-go-go-related heart potassium channel gene (hERG) and had no moderate effects on the activity of the different isoforms of liver cytochrome P450.

In other words, the invention relates to the use of fatty acid amides conjugated with phenylalkylamines (amphetamines, dopamine, etc.) for preparing a medicinal product for the prevention and/or treatment of a disease caused by fatty liver, preferably steatohepatitis.

Medical Use of the Compound of the Invention

Therefore, a first aspect of the present invention relates to the use of a compound of general formula (I) (also referred to as the compound of the invention):

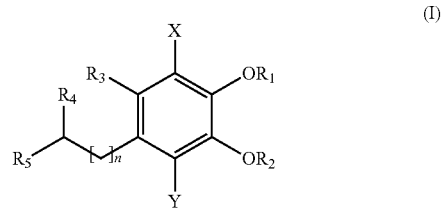

(I)

where
X and Y can independently be the same or different and are selected from H, halogen and methyl;
n is an integer from 1 to 4;
$R_1$ and $R_2$ can independently be the same or different and are selected from H and $C_1$-$C_6$ alkyl or can be bound by a single bond between the two oxygen atoms, forming a new ring;
$R_3$ is selected from H, $C_1$-$C_6$ alkyl and $C_1$-$C_4$ alkenyl;
$R_4$ is selected from H, halogen and $C_1$-$C_4$ alkyl;
$R_5$ is a compound of general formula (II):

(II)

where:
$R_6$ is selected from H and $C_1$-$C_4$ alkyl;
$R_7$ is selected from $C_8$-$C_{30}$ alkyl and $C_8$-$C_{30}$ alkenyl;
or any of the salts thereof, preferably any pharmaceutically acceptable salt, pharmaceutically acceptable esters, tautomers, polymorphs, hydrates, or an isomer, prodrugs, derivatives, solvates or analogues, or any of the combinations thereof, in the preparation of a medicinal product for the prevention, relief and/or treatment of fatty liver or a pathological condition or disease caused by fatty liver.

In a preferred embodiment of this aspect of the invention, the disease caused by fatty liver is steatohepatitis.

In a preferred embodiment of this aspect of the invention, the compound is used in the preparation of a medicinal product for the prevention, relief and/or treatment of a disease caused by non-alcoholic fatty liver disease (NAFLD), more preferably non-alcoholic steatohepatitis (NASH).

In the present invention, "disease caused by non-alcoholic fatty liver disease (NAFLD)" describes a wide range of conditions caused by an excessive accumulation of fat in the form of triglycerides (steatosis) in the liver (histologically >5% of hepatocytes). In addition to the excessive fat (steatohepatitis), a subgroup of patients with NAFLD suffers from hepatocyte damage and inflammation. Histologically speaking, this condition, called "non-alcoholic steatohepatitis (NASH)", is virtually indistinguishable from alcoholic steatohepatitis (ASH). While the simple steatosis observed in NAFLD does not result in an increase in short-term morbidity or mortality, the progress of this condition to NASH drastically increases the risk of cirrhosis, liver failure, and hepatocellular carcinoma (HCC). Cirrhosis due to NASH is an increasingly common reason for liver transplant. Although liver-related morbidity and mortality are very high in patients with NASH, the correlation is even greater with cardiovascular pathology-related morbidity and mortality.

In the present invention, the term "alkyl" refers to radicals that have linear or branched hydrocarbon chains having 1 to 10 carbon atoms, preferably 1 to 4, and that bind to the rest of the molecule by means of a single bond, for example, methyl, ethyl, n-propyl, i-propyl, n-butyl, tert-butyl, sec-butyl, n-pentyl, n-hexyl, etc. The alkyl groups can be optionally substituted with one or more substituents such as halogen, hydroxyl, alcoxyl, carboxyl, carbonyl, cyano, acyl, alcoxycarbonyl, amino, nitro, mercapto and alkylthio.

The term "alkenyl" refers to a radicals having hydrocarbon chains containing one or more carbon-carbon double bonds, for example, vinyl, 1-propenyl, allyl, isoprenyl, 2-butenyl, 1,3-butadienyl, etc. Alkenyl radicals can be optionally substituted with one or more substituents such as halo, hydroxyl, alcoxyl, carboxyl, cyano, carbonyl, acyl, alcoxycarbonyl, amino, nitro, mercapto and alkylthio.

The term "halogen" refers to a fluorine, chlorine, bromine or iodine.

In a preferred embodiment of this aspect of the invention, X and Y can independently be the same or different and are selected from H and $CH_3$.

In a preferred embodiment of this aspect of the invention, n is an integer selected from 1 or 3, more preferably 1.

In another preferred embodiment of this aspect of the invention, $R_1$ and $R_2$ can independently be the same or different and are selected from H and $CH_3$ or can be bound by a single bond between the two oxygen atoms, forming a new ring.

In another preferred embodiment of this aspect of the invention, $R_3$ is selected from H and $C_1$-$C_3$ alkyl, and is more preferably H.

In another preferred embodiment of this aspect of invention, $R_4$ is selected from H and $CH_3$, and is more preferably $CH_3$.

In another preferred embodiment of this aspect of the invention, $R_5$ is a compound of formula (II):

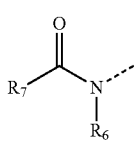

(II)

where $R_6$ is selected from H and $CH_3$ and $R_7$ is a $C_{15}$-$C_{25}$ alkenyl group.

In another preferred embodiment of this aspect of the invention, $R_7$ has a number of unsaturations between 1 and 6, more preferably between 1 and 4.

In another preferred embodiment of the invention, the compound of general formula (I) relates to a compound which is selected from the following group:

Formula (III)

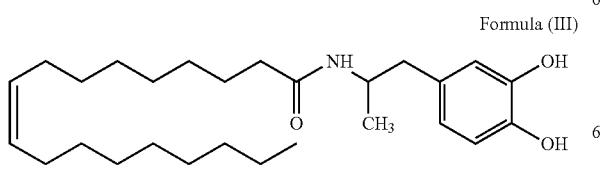

Formula (IV)

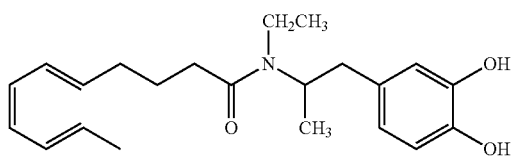

Formula (V)

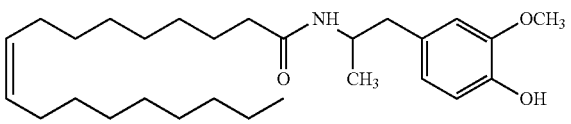

Formula (VI)

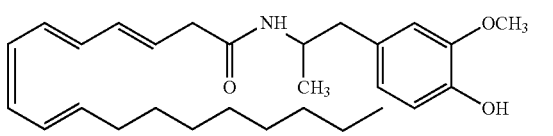

Formula (VII)

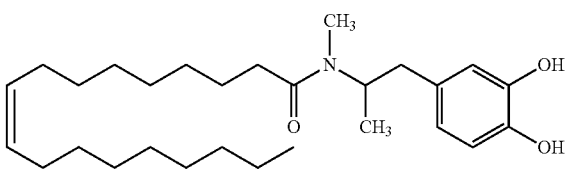

Formula (VIII)

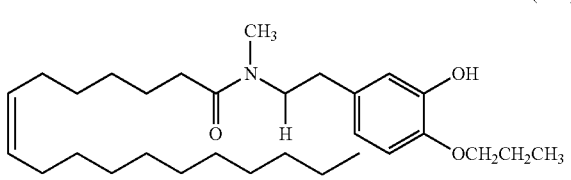

Formula (IX)

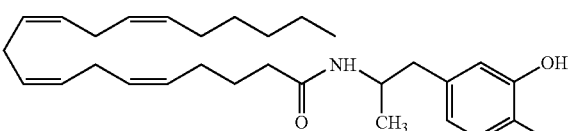

Formula (X)

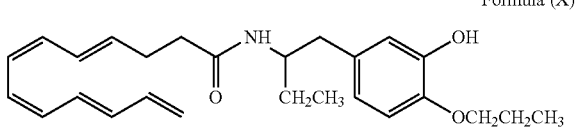

Formula (XI)

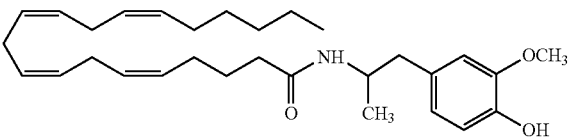

Formula (XII)

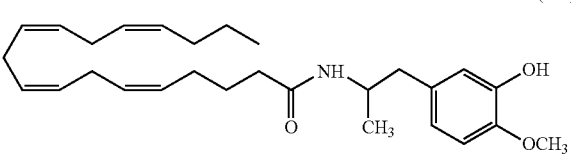

-continued

Formula (XIII)

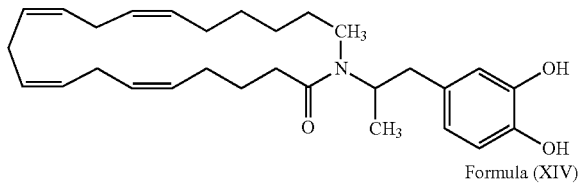

Formula (XIV)

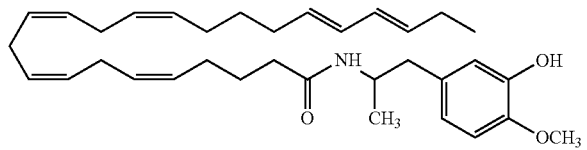

Formula (XV)

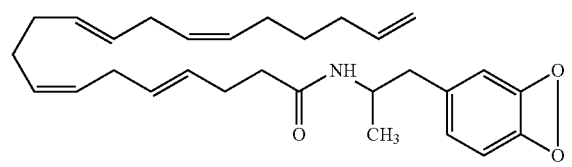

or any of the salts thereof, preferably any pharmaceutically acceptable salt, pharmaceutically acceptable esters, tautomers, polymorphs, hydrates, or an isomer, prodrugs, derivatives, solvates or analogues, or any of the combinations thereof, or any of the combinations thereof.

In a preferred embodiment of this aspect of the invention, the compound is N-(1-(3,4-dihydroxyphenyl)propan-2-yl) oleamide (OLHHA).

Formula (III)

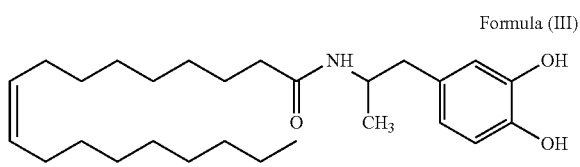 [SMILES: CCCCCCCC/C=C\CCCCCCCC(=O)NC(C)Cc1ccc(O)c(O)c1]

The compounds of the present invention represented by formula (I) can include isomers, depending on the presence of multiple bonds, including optical isomers or enantiomers, depending on the presence of chiral centers. The individual isomers, enantiomers or diastereoisomers and the mixtures thereof fall within the scope of the present invention, i.e., the term isomer also refers to a any mixture of isomers, such as diastereomers, racemates, etc., even the optically active isomers thereof or mixtures in different proportions thereof. The individual enantiomers or diastereoisomers, as well as their mixtures, can be separated by means of conventional techniques.

The prodrugs of the compounds of formula (I) also fall within the scope of this invention. As it is used herein, the term "prodrug" includes any derivative of a compound of formula (I), for example, and in a non-limiting manner: esters (including carboxylic acid esters, amino acid esters, phosphate esters, sulfonate esters of metal salts, etc.), carbamates, amides, etc., which when administered to an individual can be converted directly or indirectly into said compound of formula (I) in the mentioned individual. Advantageously, said derivative is a compound which increases the bioavailability of the compound of formula (I) when administered to an individual or promotes the release of the compound of formula (I) in a biological compartment.

The nature of said derivative is not critical provided that it can be administered to an individual and can provide the compound of formula (I) in a biological compartment of an individual. Said prodrug can be prepared by means of conventional methods known by the persons skilled in the art.

As it is used herein, the term "derivative" includes compounds that are pharmaceutically acceptable, i.e., derivatives of the compound of formula (I) which can be used for preparing a medicinal product or food compositions, as derivatives that are not pharmaceutically acceptable, since they may be useful for preparing pharmaceutically acceptable derivatives.

The compounds of the invention can be in crystalline form as free compounds or solvates. In this sense, as it is used herein the term "solvate" includes solvates that are pharmaceutically acceptable, i.e., solvates of the compound of formula (I) which can be used for preparing a medicinal product, and solvates that are not pharmaceutically acceptable, which may be useful for preparing pharmaceutically acceptable solvates or salts. The nature of the pharmaceutically acceptable solvate is not critical provided that it is pharmaceutically acceptable. In a particular embodiment, the solvate is a hydrate. The solvates can be obtained by conventional solvation methods known by the persons skilled in the art.

For application in therapy, the compounds of formula (I), the salts, prodrugs or solvates thereof, will preferably be in a pharmaceutically acceptable or substantially pure form, i.e., having a pharmaceutically acceptable level of purity, excluding normal pharmaceutical additives such as diluents and carriers, and not including material considered toxic at normal dosage levels. The levels of purity for the active ingredient are preferably greater than 50%, more preferably greater than 70%, and even more preferably greater than 90%. In a preferred embodiment, the levels of purity of the compound of formula (I), or of the salts, solvates or prodrugs thereof, are greater than 95%.

Pharmaceutical Composition and Dosage Form of the Invention

A second aspect of the invention relates to the use of a pharmaceutical composition comprising at least one compound of the invention, or a tautomer, a pharmaceutically acceptable salt, a derivative or a prodrug thereof, together with a pharmaceutically acceptable carrier, an excipient or a vehicle, in the preparation of a medicinal product for the prevention, relief and/or treatment of fatty liver or a pathological condition or disease caused by fatty liver.

In a preferred embodiment of this aspect of the invention the disease caused by fatty liver is steatohepatitis.

In another preferred embodiment of this aspect of the invention, the pharmaceutical composition of the invention is used in the preparation of a medicinal product for the prevention, relief and/or treatment of a disease caused by non-alcoholic fatty liver disease (NAFLD), preferably non-alcoholic steatohepatitis (NASH).

In another preferred embodiment of this aspect of the invention, the pharmaceutical composition of the invention is used for the prevention, relief or treatment of a disease caused by alcoholic fatty liver disease (AFLD), preferably alcoholic steatohepatitis (ASH).

The pharmaceutically acceptable adjuvants and vehicles which can be used in said compositions are adjuvants and vehicles known by the persons skilled in the art and commonly used for preparing therapeutic compositions.

In the sense used in this description, the expression "therapeutically effective amount" refers to the amount of the agent or compound which is capable of developing the therapeutic action determined by its pharmacological properties, calculated to produce the desired effect and will be generally determined, among other causes, by the characteristics of the compounds themselves, including the age, the condition of the patient, the severity of the impairment or disorder, and the route and frequency of administration.

The compounds described in the present invention, the salts, prodrugs and/or solvates thereof, as well as the pharmaceutical compositions containing them can be used together with other additional drugs or active ingredients, to provide a combination therapy. Said additional drugs can be part of the same pharmaceutical composition or can alternatively be provided in the form of a separate composition for simultaneous or non-simultaneous administration with respect to the pharmaceutical composition comprising a compound of formula (I), or a salt, prodrug or solvate thereof.

Therefore, in another preferred embodiment the pharmaceutical composition further comprises another active ingredient. More preferably, the active ingredient is selected from the list consisting of: vitamin E, vitamin C, betaine, N-acetylcysteine, ursodeoxycholic acid, and other antioxidants.

As it is used herein, the term "active ingredient", "active substance", "pharmaceutically active substance" or "pharmaceutically active ingredient" means any component that may provide a pharmacological activity or another different effect in the diagnosis, cure, mitigation, treatment, or prevention of a disease, or that affects the body structure or function of humans or other animals. The term includes those components that promote a chemical change in the production of the drug and are present in the drug in an envisaged modified form, providing the specific activity or effect.

Another aspect of the invention relates to a dosage form, hereinafter dosage form of the invention, comprising the compound of the invention or the composition of the invention.

In this specification, "dosage form" is understood to be the mixture of one or more active ingredients with or without additives having physical characteristics for suitable dosing, preservation, administration and bioavailability.

In another preferred embodiment of the present invention, the compositions and dosage forms of the invention are suitable for oral administration, in solid or liquid form. The possible forms for oral administration are tablets, capsules, syrups or solutions and can contain conventional excipients known in the pharmaceutical sector, such as binding agents (e.g., syrup, acacia, gelatin, sorbitol, tragacanth or polyvinyl pyrrolidone), fillers (e.g., lactose, sugar, cornstarch, calcium phosphate, sorbitol or glycine), disintegrants (e.g., starch, polyvinyl pyrrolidone or microcrystalline cellulose) or a pharmaceutically acceptable surfactant such as sodium lauryl sulfate. Other dosage forms can be colloidal systems including, among others, nanoemulsions, nanocapsules and polymeric nanoparticles.

The compositions for oral administration can be prepared using conventional Galenic Pharmacy methods, such as mixture and dispersion. Tablets can be coated following methods known in the pharmaceutical industry.

The compositions and dosage forms can be adapted for parenteral administration, such as sterile solutions, suspensions, or lyophilisates of the products of the invention, using the suitable dose. Suitable excipients, such as pH buffering agents or surfactants, can be used.

The aforementioned formulations can be prepared using conventional methods, such as those described in the pharmacopoeias of different countries and in other reference texts.

As it is used herein, the term "medicinal product" refers to any substance used for the prevention, diagnosis, relief, treatment or cure of diseases in humans and animals.

The compounds, compositions or dosage forms of the present invention can be administered by means of any suitable method, such as intravenous infusion and oral, topical or parenteral routes. Oral administration is preferred due to it being convenient for patients and to the chronic character of the diseases to be treated.

The administered amount of a compound of the present invention will depend on the relative efficacy of the chosen compound, the seriousness of the disease to be treated and the weight of the patient. However, the compounds of this invention will be administered once or more times a day, for example 1, 2, 3 or 4 times a day, with a total dose between 0.1 and 1000 mg/kg/day. It is important to take into account that it may be necessary to introduce variations in the dose, depending on patient's age and condition, as well as modifications in the route of administration.

The compounds and compositions of the present invention can be used together with other medicinal products in combined therapies. The other drugs can be part of the same composition or of another different composition, for administration thereof at the same time or at different times.

Food Composition

A third aspect of the invention relates to a food composition such as a nutraceutical composition or a medical food-type composition, hereinafter food composition of the invention, comprising at least one of the compounds of formula (I).

The food composition of the invention comprises the compound of the invention in an amount effective for the prevention, relief and/or treatment of a disease caused by non-alcoholic fatty liver disease (NAFLD), and preferably for the prevention, relief and treatment of non-alcoholic steatohepatitis (NASH), in mammals, including a human being. Preferred food compositions are selected from the list consisting of: a beverage, milk, yogurt, cheese, fermented milk, aromatized milk beverage, soy milk, ready-made cereals, bread, pastry, butter, margarine, sauces, oils for frying, vegetable oils, corn oil, olive oil, soybean oil, palm oil, sunflower oil, cotton seed oil, condiments, dressings for salads, fruit juices, syrups, desserts, glazings and fillings, frozen soft products, candy, chewing gums and intermediate foods. The food composition of the invention can be a nutritional or dietary supplement. In another preferred embodiment, the nutritional or dietary supplement comprises a sterile composition containing the compound of the invention, preferably provided with a gastric acid-resistant coating, being a delayed-release composition. In another preferred embodiment, the food composition, including the compound of the invention and/or the nutritional or dietary supplement, comprises suitable "carriers" such as diluents, adjuvants, excipients or vehicles with which the compound of the invention is administered. Suitable excipients include, but are not limited to, starch, glucose, fructose, lactose, sucrose, gelatin, malt, rice, flour, calcium sulfate, silica gel, sodium stearate, glycerol monostearate, talc, sodium chloride, skim milk powder, glycerol, propylene, glycol, water, ethanol, and the like. Such nutritional supplements can be used for combating liver problems, and help a mammal, preferably a human being, to maintain health or a healthy lifestyle.

A fourth aspect of the invention relates to the use of the food composition of the invention for the prevention, relief or treatment of fatty liver or a pathological condition or disease caused by fatty liver, preferably steatohepatitis in mammals, preferably human beings. Alternatively, it relates to the use of the food composition of the invention for the prevention and/or treatment of fatty liver or a pathological condition or disease caused by fatty liver, preferably steatohepatitis.

In a preferred embodiment of this aspect of the invention, the food composition of the invention is used for the prevention, relief or treatment of a disease caused by non-alcoholic fatty liver disease (NAFLD), preferably non-alcoholic steatohepatitis (NASH).

In another preferred embodiment of this aspect of the invention, the food composition of the invention is used for the prevention, relief or treatment of a disease caused by alcoholic fatty liver disease (AFLD), preferably alcoholic steatohepatitis (ASH).

The term "treatment" as understood in the present invention refers to combating the effects caused by a pathological condition or disease of interest in a subject (preferably a mammal, and more preferably a human), including:

(i) inhibiting the pathological condition or disease, i.e., stopping its development;

(ii) alleviating the pathological condition or disease, i.e., causing the regression of the pathological condition or disease or its symptomatology;

(iii) stabilizing the pathological condition or disease.

The term "prevention" as understood in the present invention consists of preventing the onset of the disease, i.e., preventing the pathological condition or disease from occurring in a subject (preferably a mammal, and more preferably a human), particularly when said subject has a predisposition for the pathological condition.

The method of obtaining a compound of formula (I) could comprise the following steps:

a) conjugating a compound of general formula (III) and benzyl chloroformate to yield a new compound of general formula (IV), comprising the following reaction:

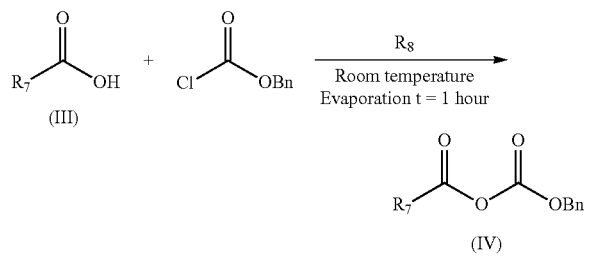

where $R_7$ is selected from $C_8$-$C_{30}$ alkyl and $C_8$-$C_{30}$ alkenyl and $R_8$ is selected from $NH_3$, $NH_2$—$CH_3$, $NH_2$—$CH_2$—$CH_3$, $NH$—$(CH_3)_2$, $N$—$(CH_3)_3$ $NH$—$(CH_2$—$CH_3)_2$ and $N$—$(CH_2$—$CH_3)_3$;

b) reacting the compound of general formula (IV) with a compound of general formula (V) to yield the compound of general formula (I) using dimethylformamide as solvent:

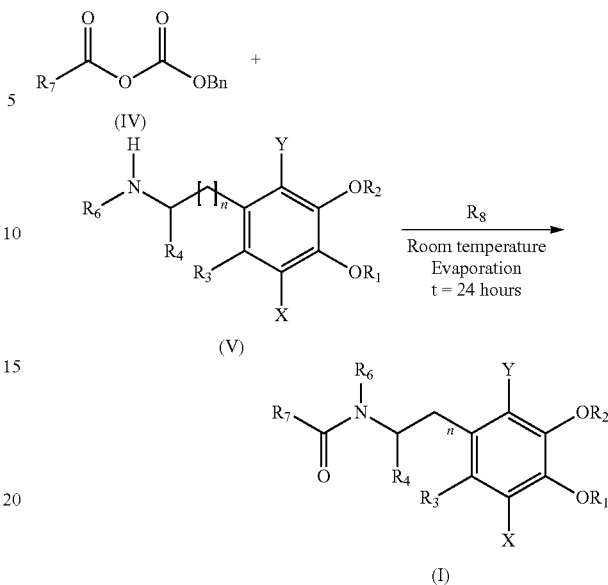

where

X and Y can independently be the same or different and are selected from H, halogen and methyl;

n is an integer from 1 to 4;

$R_1$ and $R_2$ can independently be the same or different and are selected from H and $C_1$-$C_6$ alkyl or can be bound by a single bond between the two oxygen atoms, forming a new ring;

$R_3$ can be selected from H, $C_1$-$C_6$ alkyl and $C_1$-$C_4$ alkenyl;

$R_4$ can be selected from H, halogen and $C_1$-$C_4$ alkyl;

$R_6$ can be selected from H and $C_1$-$C_4$ alkyl;

$R_7$ can be selected from $C_8$-$C_{30}$ alkyl and $C_8$-$C_{30}$ alkenyl;

$R_8$ can be selected from $NH_3$, $NH_2$—$CH_3$, $NH_2$—$CH_2$—$CH_3$, $NH$—$(CH_3)_2$, $N$—$(CH_3)_3$ $NH$—$(CH_2$—$CH_3)_2$ and $N$—$(CH_2$—$CH_3)_3$;

c) evaporating dimethylformamide and performing extraction with ethyl acetate and water;

d) treating the organic phase with sodium sulfate anhydrous and evaporating the solvent;

e) purifying the compound of formula (I) by silica gel column FLASH chromatography.

The compounds of general formula (I) were synthesized according to the previously described methodology (*ChemMedChem*.2010, 5(10), 1781-1787).

Throughout the description and the claims, the word "comprises" and variants thereof do not seek to exclude other features, techniques, additives, components or steps. For the persons skilled in the art, other objects, advantages and features of the invention will be inferred in part from the description and in part of the practice of the invention. The following examples and drawings are provided by way of illustration and do not seek to limit the present invention.

EXAMPLES OF THE INVENTION

All the experiments were carried out in obese (fa/fa) and thin (Fa/?) male Zucker rats 8-9 weeks of age. The animals were placed in individual cages in a room with controlled temperature, humidity and lighting (light/darkness cycles of 12 hours), and with free access to food and water (standard laboratory diet).

OLHHA was dissolved in a vehicle containing 5% Tween 80 in saline and intraperitoneally (i.p.) administered at a dose of 5 mg/kg (volume of 1 ml/kg body weight) at the beginning of the light cycle (9:00 am-10:00 am) for 15 consecutive days. Two hours after the last injection, the animals were euthanized using sodium pentobarbital (50 mg/kg, i.p.) and blood and liver samples were extracted. The blood was centrifuged at 2100×g for 8 minutes at 4° C. and the obtained plasma was kept at −80° C. for subsequent analysis. The liver samples were also stored at −80° C.

Example 1. Effects of Chronic Treatment with OLHHA on Body Weight Gain and Intake in Zucker Rats Animals received an injection (i.p.) of vehicle or OLHHA (5 mg/kg) daily for 15 consecutive days. For this experiment, 8 rats were used per group. The total body weight gain (g) and the accumulated food intake (g/kg of body weight) were evaluated daily.

In thin rats, OLHHA caused a significant inhibition of body weight gain and a significant reduction in accumulated food intake starting on the fifth day of treatment in comparison with rats treated with the vehicle (FIGS. 1A, 1B). In obese rats, the treatment did not cause any effect on body weight gain and accumulated food intake (FIGS. 10, 1D). The results are expressed as means±SEM (n=8 animals per group). The data was analyzed using two-way ANOVA (genotype and treatment) and Bonferroni post-hoc analysis. *$p<0.05$, $p<0.01$ and *$p<0.001$ denote significant differences in comparison with the group treated with the vehicle.

Example 2. Effects of Chronic Treatment with OLHHA on the Liver Fat Content and the Plasma Triglyceride Level of Zucker Rats The total liver fat content and the plasma triglyceride level were evaluated in thin and obese Zucker rats after a 15-day treatment with OLHHA (5 mg/kg, once a day). The samples for lipid analysis were obtained 2 hours after the last injection.

The Bligh & Dyer method (Bligh and Dyer, 1959) was followed for liver fat quantification. Total lipids were extracted using an extraction mixture made up of chloroform:methanol in a proportion of 2:1 (v/v); furthermore, since most lipids contain oxidation-sensitive double bonds, 0.025% of the antioxidant butylhydroxytoluene was added. The liver samples were homogenized and centrifuged twice at 2800×g for 10 minutes at 4° C. Lipids, which were concentrated in the lower organic phase, were extracted and dried under nitrogen flow. The fat content was expressed as % of tissue weight.

A colorimetric method-based commercial kit (Randox Laboratories) which determines the triglyceride content after an enzymatic hydrolysis with lipases was used for determining circulating triglycerides.

Figure 2:
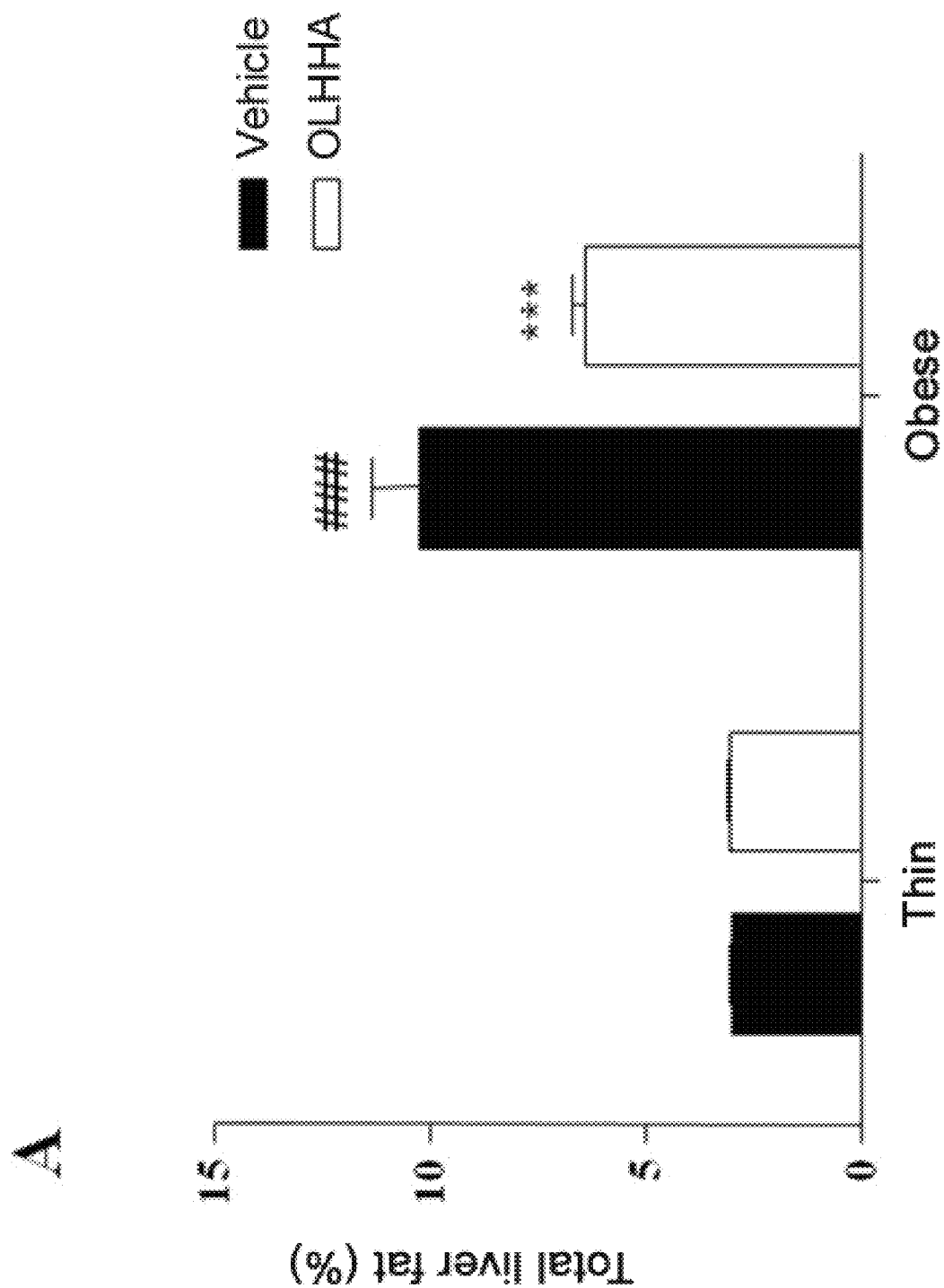
FIG. 2 shows the effects of chronic treatment with OLHHA on the liver fat content and the plasma triglyceride level of Zucker rats.
Figure 2:
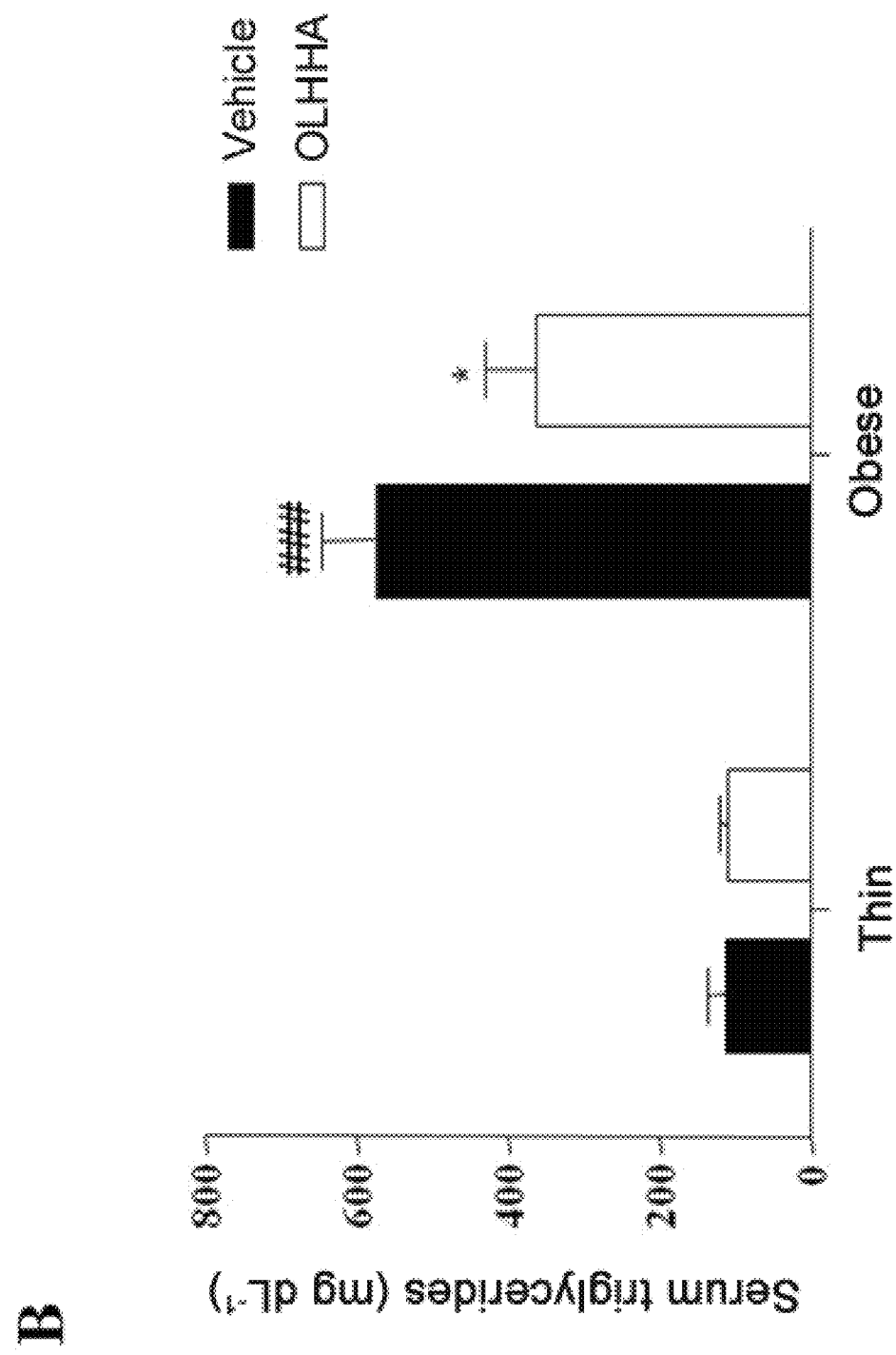

Obese rats showed a three-fold increase in total liver fat content in comparison with thin rats (FIG. 2A), as well as a prominent increase (five-fold) in circulating triglycerides (FIG. 2B). In both cases, treatment with OLHHA prevented these increases. The results are expressed as means±SEM (n=8 animals per group). The data was analyzed using two-way ANOVA (genotype and treatment) and Bonferroni post-hoc analysis. *$p<0.05$ and ***$p<0.001$ denote significant differences in comparison with the group treated with the corresponding vehicle. ####$p<0.001$ denotes significant differences in comparison with the thin group treated with the vehicle.

OLHHA reduces liver fat levels and plasma triglyceride levels in obese animals with fatty liver.

Example 3. Effects of Chronic Treatment with OLHHA on the Hepatic Transaminase Level in Obese Rats Commercial kits were used for determining hepatic serum transaminases and they were analyzed in a Hitachi 737 automatic biochemistry analyzer.

Figure 3:
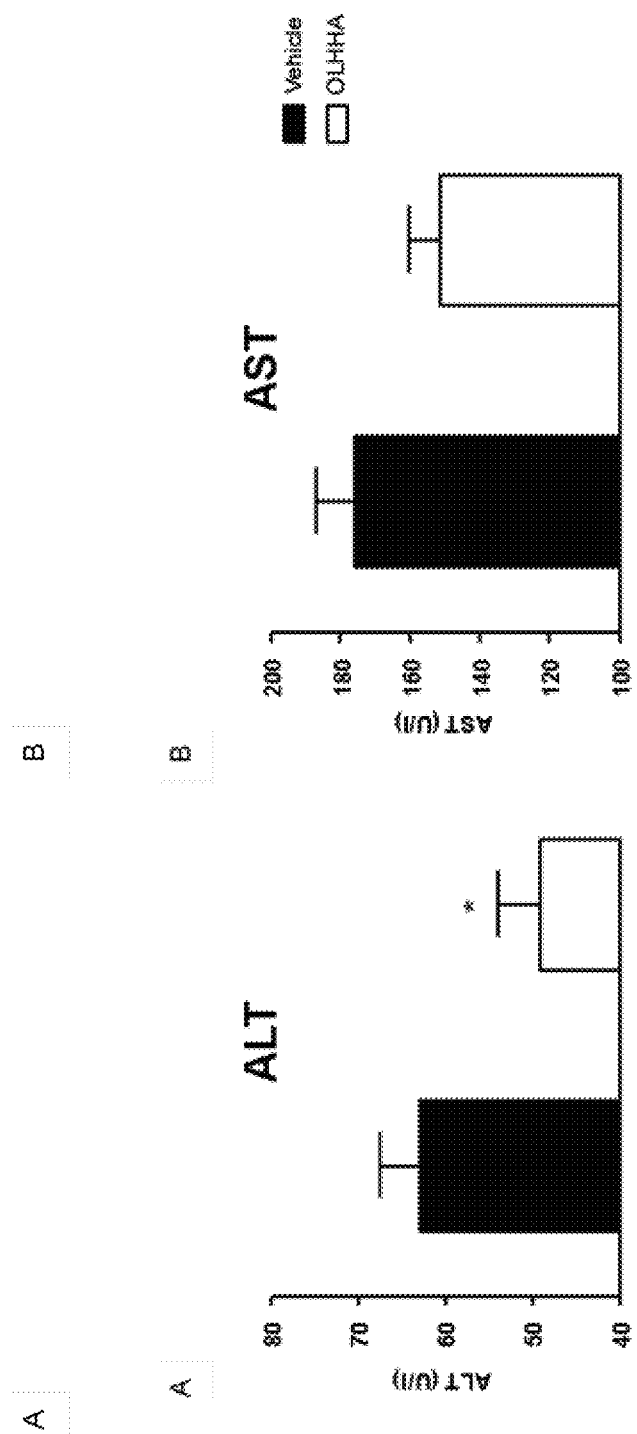
FIG. 3 shows the effects of chronic treatment with OLHHA on the transaminase level in obese rats.
Figure 3:
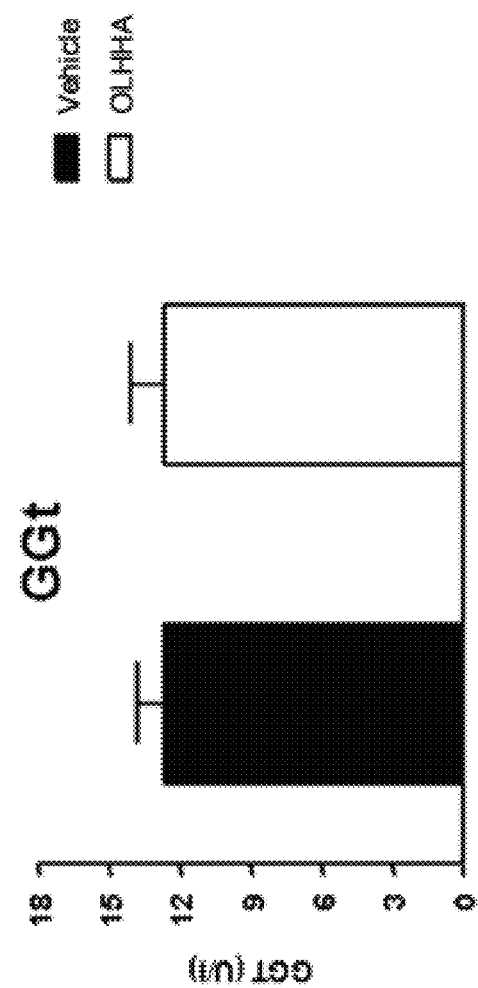

The administration of 5 mg/kg (i.p.) of OLHHA for 15 days caused a reduction in the levels of transaminase enzymes: alanine aminotransferase (ALT) (FIG. 3A) and aspartate aminotransferase (AST) (FIG. 3B) in obese animals, being statistically significant in the case of ALT (*$p<0.05$). These enzymes are liver cell damage indicators. ALT and AST are enzymes in liver cells that penetrate the blood circulation in the event of liver cell damage. It is believed that ALT is a more specific liver inflammation indicator, whereas AST may be elevated in diseases affecting other organs, such as the heart or the muscle. ALT and the AST are often used for assessing the progress of chronic hepatitis.

With respect to the gamma-glutamyl transpeptidase (GGt) enzyme (FIG. 3C), no effect was observed with respect to the group treated with the vehicle. GGt is an enzyme indicating obstruction in the biliary system, be it in the liver or in the major bile ducts outside this organ. GGt increases in a large number of disorders affecting bile drainage, such as in the event of a liver disease caused by alcohol or drugs, which leads to bile flow blockage in the smaller ducts inside the liver.

OLHHA improves the hepatic plasma transaminase profile with a drop in ALT and AST.

Example 4. Effects of Chronic Treatment with OLHHA on the Pro-Inflammatory Cytokine Level in Obese Rats Circulating IL-6 and TNF-α levels were measured by means of ELISAs using commercial kits (Abcam).

Figure 4:
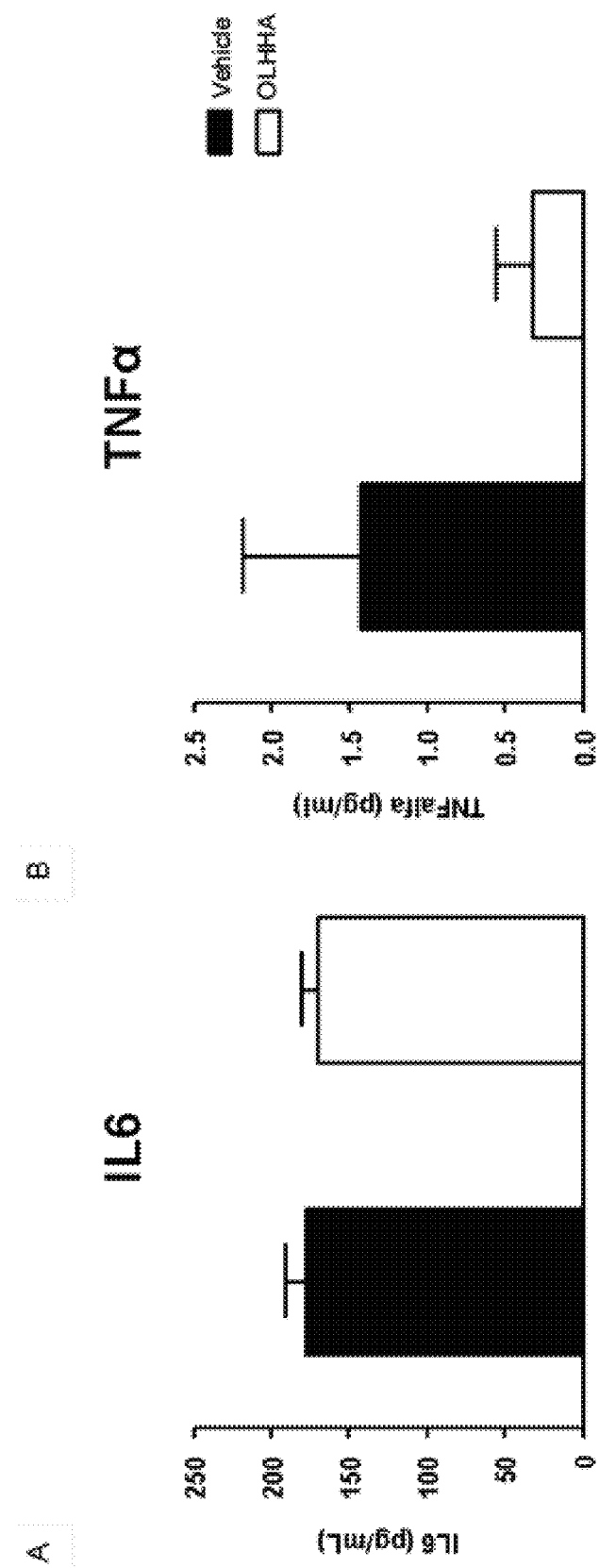
FIG. 4 shows the effects of chronic treatment with OLHHA on the pro-inflammatory cytokine level in obese rats.

The administration of 5 mg/kg (i.p.) of OLHHA for 15 days induced a drop in pro-inflammatory cytokines (FIG. 4), specifically TNF-α although it did not reach a degree of significance. Nevertheless, no changes were detected on plasma IL6 levels. Many pathologies, including obesity and related disorders such as hepatic steatosis, are characterized by having a pro-inflammatory profile through cytokines and immune cells.

OLHHA improves the pro-inflammatory profile of obese animals with a reduction of plasma TNF-α.

Example 5. Effects of Chronic Treatment with OLHHA on the Kidney Function-Related Plasma Protein Level in Obese Rats Commercial kits were used for determining serum creatinine and urea and they were analyzed in a Hitachi 737 automatic biochemistry analyzer.

Figure 5:
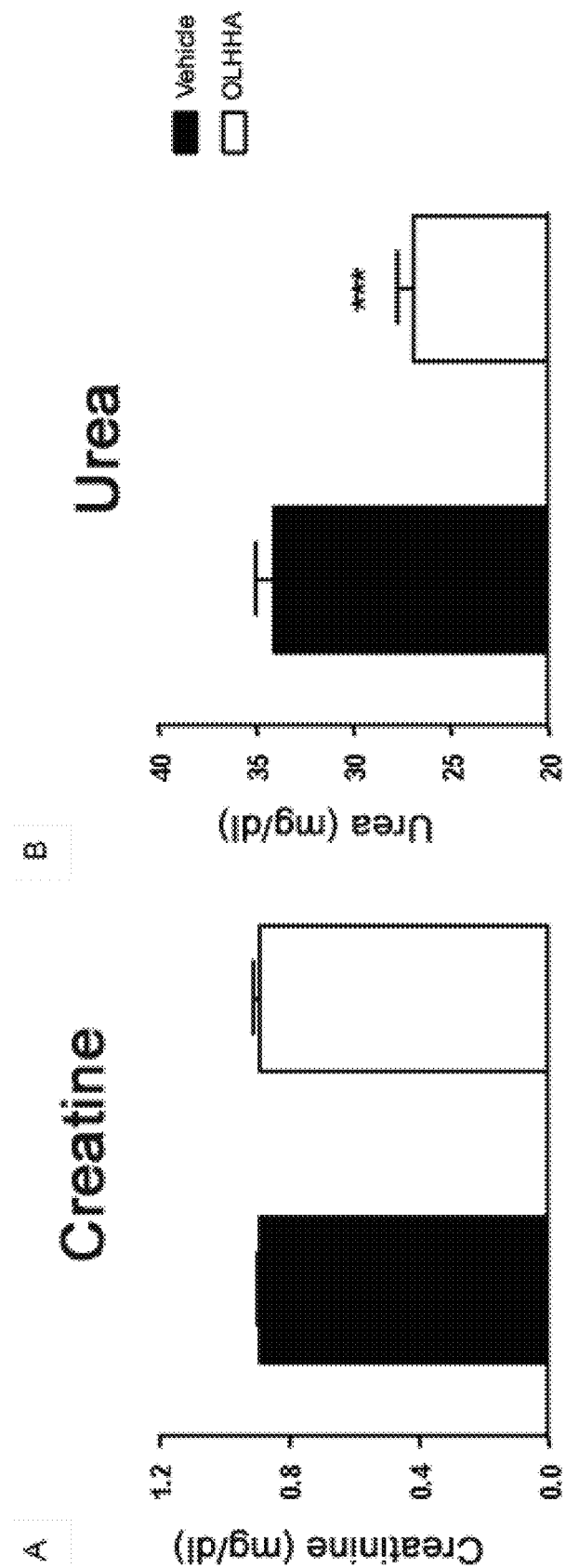
FIG. 5 shows the effects of chronic treatment with OLHHA on the kidney function-related plasma protein level in obese rats.

The administration of 5 mg/kg (i.p.) of OLHHA for 15 days did not affect creatinine levels (FIG. 5A) but caused a significant reduction in urea levels (***$p<0.001$) with respect to animals treated with the vehicle (FIG. 5B). This reduction in urea concentration is related with the normalization of liver activity and protein catabolism.

Creatinine and urea are two substances present in the blood and are usually determined when kidney function is to be evaluated.

Measuring creatinine is a simple test and the most common indicator of kidney function, i.e., its filtration capacity. In terms of urea, it is the final result of protein metabolism and it is formed in the liver from protein decomposition.

OLHHA improves kidney function through a reduction of increased plasma urea levels.

Effects of Chronic Treatment with OLHHA on Gene Expression in the Liver of Zucker Rats For isolating total RNA from the liver, the samples were homogenized in Trizol and then purified using Qiagen RNeasy Minelute Cleanup Kit (selectively eliminates most molecules smaller than 200 nucleotides), also including a DNAse treatment. The total mRNA concentration was quantified using a spectrophotometer. In all the cases, the A260/280 ratio was between 1.8 and 2. Complementary DNA synthesis was carried out by reverse transcription using the Transcriptor Reverse Transcriptase kit (Transcriptor RT, Roche Diagnostic). For real-time PCR (RT-qPCR), an ABI PRISM® 7300 Real-Time PCR System (Applied Biosystems) and TaqMan probes were used. The single-product amplification was confirmed by means of analyzing the melting curves. The values of each sample were normalized with respect to the beta-actin constitutive gene. The relative quantification was calculated by means of the $\Delta\Delta Ct$ method and normalized to the control group. The Taqman probes were obtained from the rat genome database of Applied Biosystems (http://bioinfo.appliedbiosystems.com/genome-database/gene-expression.html):

| Gene | ID | GenBank No. | Amplicon length |
|---|---|---|---|
| Beta-actin | Rn00667869_m1 | NM_031144.2 | 91 |
| FAS | Rn01463550_m1 | NM_017332.1 | 148 |
| HMG-CoAR | Rn00565598_m1 | NM_013134.2 | 71 |
| ACOX | Rn01460628_m1 | NM_017340.2 | 63 |
| INSIG2 | Rn00710111_m1 | NM_178091.4 | 89 |
| NAPE-PLD | Rn01786262_m1 | NM_199381.1 | 71 |

Figure 6:
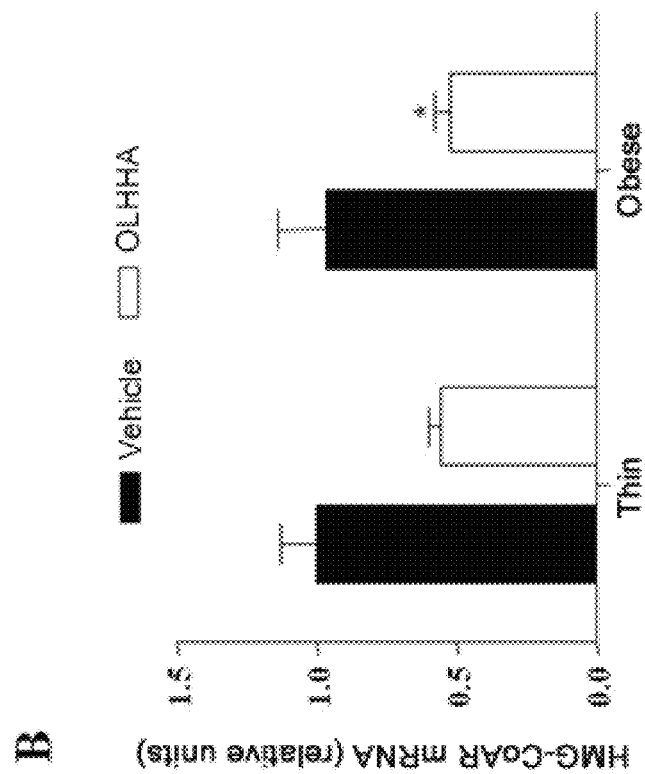
FIG. 6 shows the effects of chronic treatment with OLHHA on the gene expression of enzymes involved in lipid metabolism in the liver of Zucker rats.
Figure 6:
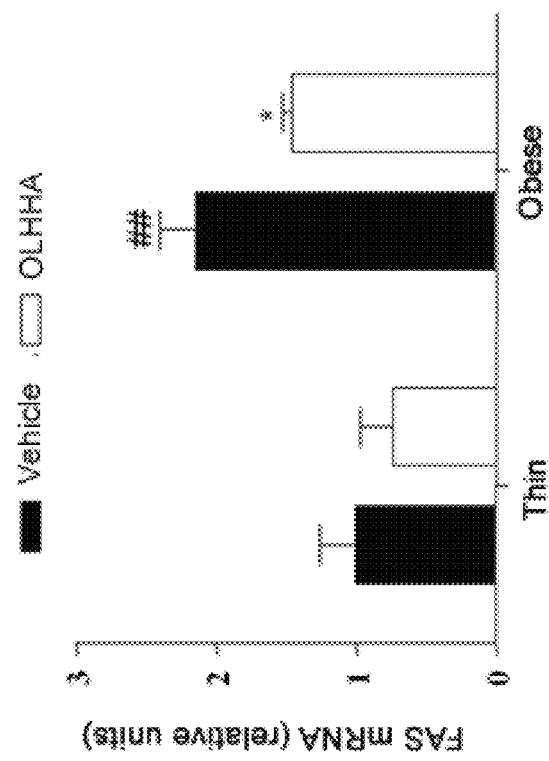
Figure 6:
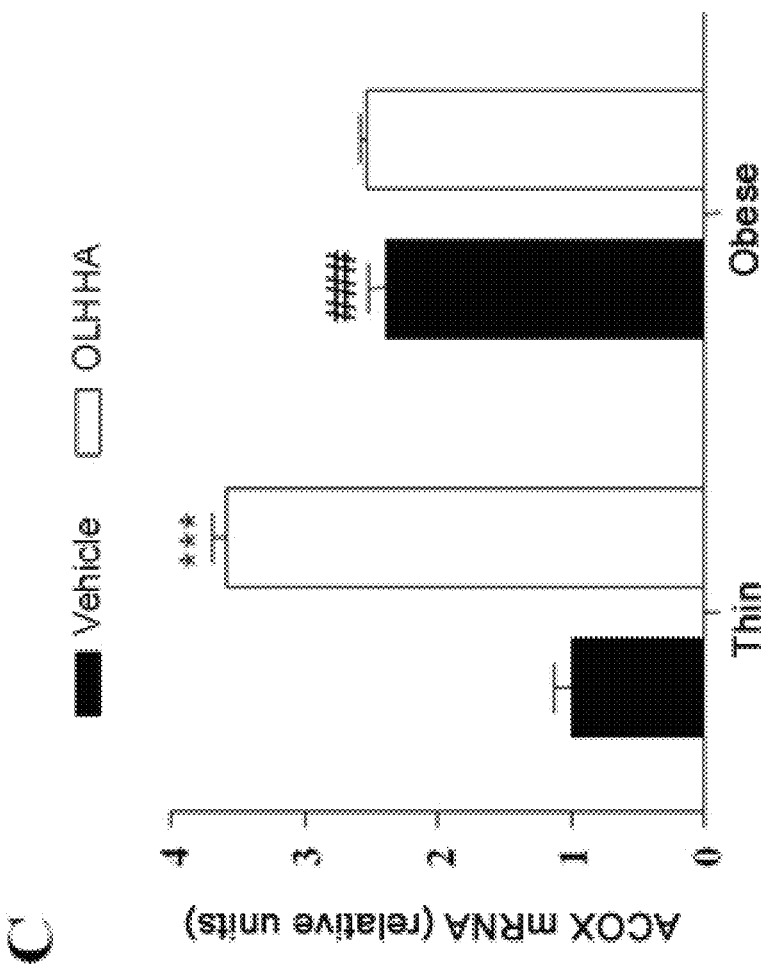

Example 6. Effects of Chronic Treatment with OLHHA on the Gene Expression of Enzymes Involved in Lipid Metabolism in the Liver of Zucker Rats The expression of the mRNA of the enzymes involved in the pathways for lipogenesis (FAS and HMG-CoAR) or fatty acid oxidation (ACOX) were analyzed using RT-qPCR in the liver of Zucker rats chronically treated with OLHHA (FIG. 6). The gene expression levels of these enzymes showed significant changes as a result of the treatment. In fact, OLHHA caused a significant reduction in the enzymes involved in fatty acid biosynthesis (FIG. 6A) and in cholesterol biosynthesis (FIG. 6B). In contrast, the compound induced a significant increase of ACOX (FIG. 6C), the enzyme involved in β-oxidation. The results are expressed as means±SEM (n=8 animals per group). The data was analyzed using two-way ANOVA (genotype and treatment) and Bonferroni post-hoc analysis. *$p<0.05$ and ***$p<0.001$ denote significant differences in comparison with the group treated with the corresponding vehicle. ##$p<0.01$ and ####$p<0.001$ denote significant differences in comparison with the thin group treated with the vehicle.

Figure 7:
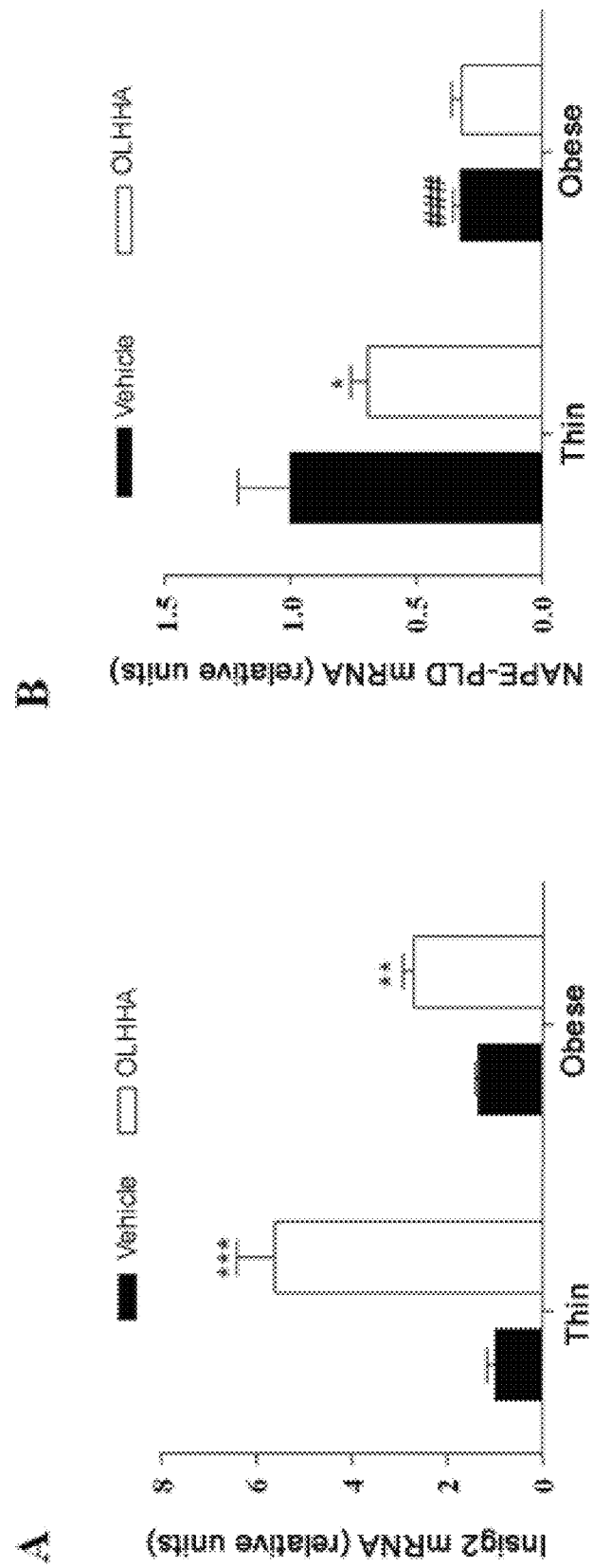
FIG. 7 shows the effects of chronic treatment with OLHHA on the gene expression of INSIG2 and NAPE-PLD in the liver of Zucker rats.

Example 7. Effects of Chronic Treatment with OLHHA on the Gene Expression of INSIG2 and NAPE-PLD in the Liver of Zucker Rats The expression of the mRNA of the INSIG2 regulating factor and of the enzyme involved in anandamide biosynthesis, NAPE-PLD, were analyzed using RT-qPCR in the liver of Zucker rats treated chronically with OLHHA (FIG. 7). OLHHA significantly increased (FIG. 7A) the expression of INSIG2, a cholesterol biosynthesis regulating factor, whereas the expression of the NAPE-PLD gene, an endocannabinoid system-related pro-lipogenic factor, was significantly reduced after treatment with OLHHA (FIG. 7B). The results are expressed as means±SEM (n=8 animals per group). The data was analyzed using two-way ANOVA (genotype and treatment) and Bonferroni post-hoc analysis. *$p<0.05$, $p<0.01$ and *$p<0.001$ denote significant differences in comparison with the group treated with the corresponding vehicle. ###$p<0.001$ denotes significant differences in comparison with the thin group treated with vehicle.

Example 8. Cardiotoxicity of OLHHA

Figure 8:
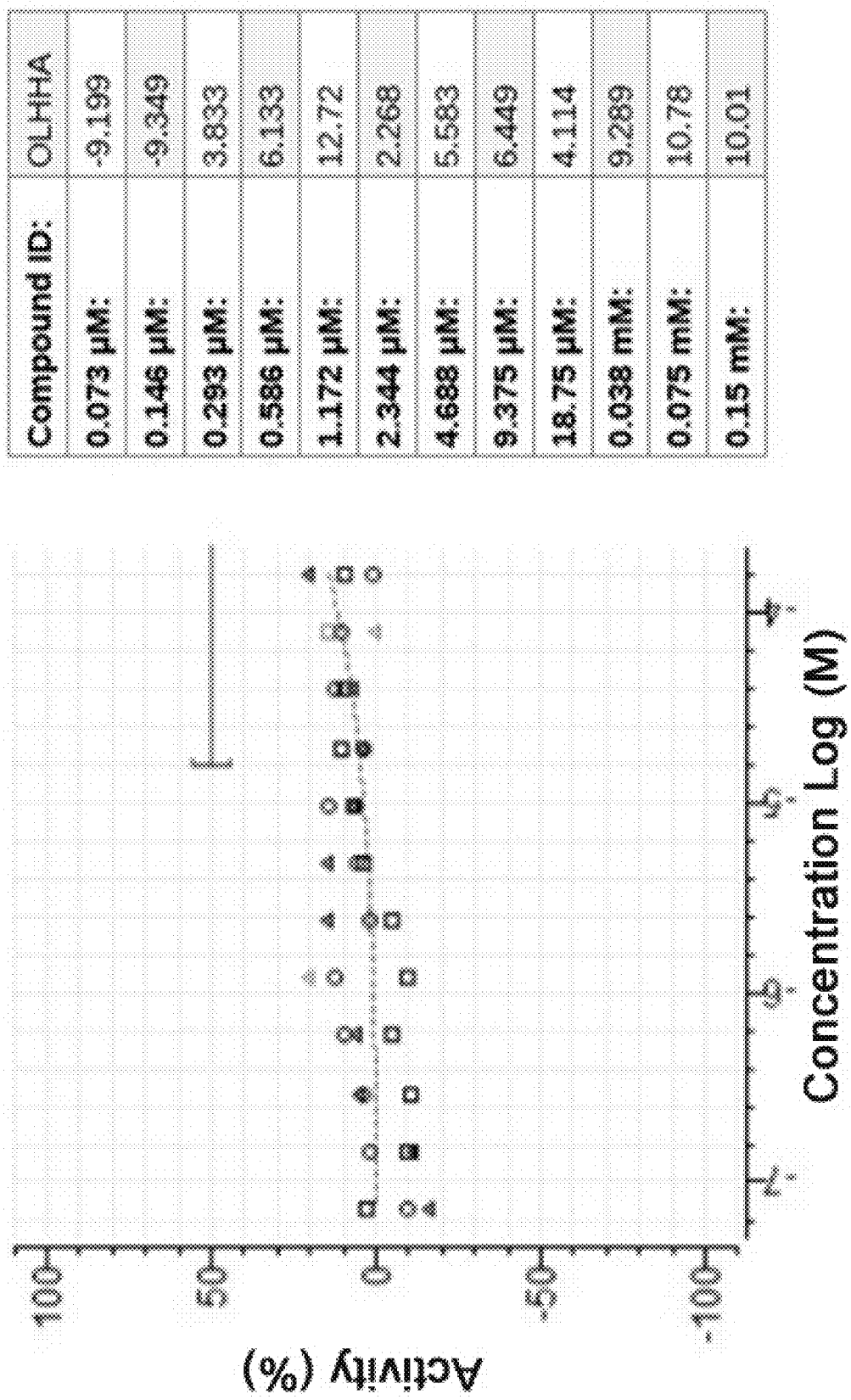
FIG. 8 shows OLHHA cardiotoxicity.

The hERG channel assay was used to identify if OLHHA may cause cardiotoxicity (FIG. 8). To better characterize the behavior of the hERG potassium channel in the presence of the compound, a functional assay based on the use of a fluorescent probe (FluxOR™, Invitrogen) emitting fluorescence after binding to thallium ions was used (Beacham et al. 2010). FluxOR™ is protected by AM groups which prevent fluorescence outside the cell. When it enters the cell, esterases in the cytosol remove the AM groups, and FluxOR™ will be converted to its active form in which it is capable of binding to thallium, which moves into the cytoplasm through the hERG channel, resulting in the emission of fluorescence. HEK293 cells expressing the hERG channel were seeded in poly-D-lysine-treated, black 96-well plates and incubated for 24 hours. After this time, the plates were washed with the assay buffer (165 mM NaCl, 4.5 mM KCl, 2 mM $CaCl_2$, 1 mM $MgCl_2$, 10 mM Hepes and 10 mM glucose, pH 7.4). Next, 20 µl of FluxOR™ dissolved in the assay buffer were added. The fluorochrome was incubated with the cells for 1 hour at room temperature. Next, the plates were washed with 50 µl of assay buffer and the compound OLHHA at a dilution of 1:200 (2 µl of OLHHA/400 µl of assay buffer) was added using an EP3 station. 20 µl from the mixture were pipetted to 3 cell plates, being assayed in triplicate in 12-point curves (dilutions of 1:2) at a maximum concentration of 150 µM. The plates were incubated with OLHHA for 30 minutes and then read in a FLIPRTETRA, which added 5 µl of stimulation buffer ($Tl_2SO_4$+$K_2SO_4$), and read the fluorescence for 120 s, which allowed analyzing channel kinetics.

In studies with HEK-293 cells expressing hERG, OLHHA did not show any activity, an $IC_{50}$ greater than 150 µM being found in comparison with standard control inhibitors ($IC_{50}$ values for amiodarone, 1.7 M; bepridil, 2.2 M; haloperidol, 1.9 µM; terfenadine, 1.0 µM). OLHHA is therefore a medicinal product with hERG inhibiting activity and can be considered a safe drug without cardiotoxicity.

OLHHA has no cardiotoxic effects.

Example 9. Pharmacokinetics of OLHHA

P450 cytochromes (CYP) are a family of enzymes that play an important role in drug metabolism. Evaluating the potential of a compound for inhibiting a CYP-specific enzyme is important in order to learn about the co-administration of compounds, which can give rise to one of the compounds inhibiting the metabolism of the other compound or to both the compounds inhibiting each other's metabolism. This can affect in vivo plasma levels and may give rise to adverse reactions or toxicity. The data of in vitro cytochrome P450 inhibition is useful in designing strategies for investigating clinical studies of drug-drug interaction.

For preparing OLHHA, it was kept in optimum conditions (at 4° C., protected from light) until use. OLHHA in solid state (powder) was dissolved in 30 mM DMSO and serially diluted with a dilution factor of 2 to obtain 8 concentrations. It is known that CYPs are inhibited by a variety of organic solvents and the effects of this inhibition can vary according to the solvent type and concentration. To that end, when DMSO is used as solvent the recommended concentration is 0.35% or less. However, most human CYPs tolerate acetonitrile. Taking this into account, serial dilutions of the compound DMSO were diluted with acetonitrile. The final organic content and the maximum dose in the assay were therefore established at 0.35% DMSO, 0.65% acetonitrile and 105 µM respectively. OLHHA was tested in triplicate. The fluorescent interference (quenching) was determined with each OLHHA dilution. Incubations were performed in linear time interval and the substrate concentration approached the Michaelis-Menten constant Km.

OLHHA did not show fluorescence or interferences in quenching. OLHHA shows much higher $IC_{50}$ values than the control inhibitors of the CYP isozymes (CYP3A4, CYP2C9 and CYP2D6).

The results are shown below:

TABLE 1

P450 cytochrome inhibition fluorometric assay using Ketoconazole as control inhibitor

| Compound | CYP3A4 $IC_{50}$ (µM) | Lower 95% CI | Upper 95% CI |
| --- | --- | --- | --- |
| OLHHA | 14.8 | 12.8 | 17.2 |
| Ketoconazole | 0.05 | 0.04 | 0.07 |

CI: confidence interval

TABLE 2

P450 cytochrome inhibition fluorometric assay using Sulfaphenazole as control inhibitor

| Compound | CYP2C9 $IC_{50}$ (µM) | Lower 95% CI | Upper 95% CI |
| --- | --- | --- | --- |
| OLHHA | 6.8 | 5.9 | 7.8 |
| Sulfaphenazole | 0.2 | 0.2 | 0.3 |

CI: confidence interval

TABLE 3

P450 cytochrome inhibition fluorometric assay using Quinidine as control inhibitor

| Compound | CYP2D6 $IC_{50}$ (µM) | Lower 95% CI | Upper 95% CI |
| --- | --- | --- | --- |
| OLHHA | 23.3 | 21.4 | 25.3 |
| Quinidine | 0.02 | 0.01 | 0.02 |

CI: confidence interval

Strong inhibitors $IC_{50}$<1 µM
Moderate inhibitors 1 µM<$IC_{50}$<10 µM
Weak inhibitors $IC_{50}$>10 µM

TABLE 4

Degree of inhibition of OLHHA

| Compound | CYP3A4 Inhibitor category | CYP2C9 Inhibitor category | CYP2D6 Inhibitor category |
| --- | --- | --- | --- |
| OLHHA | Weak | Moderate | Weak |

OLHHA can therefore be considered a moderate/weak CYP inhibitor, indicating a good pharmacokinetic profile whereby it does not interact with other drugs and does not have adverse effects.

Example 10. Histological Evaluation of the Effect of Chronic Treatment with OLHHA on Fatty Liver in Obese Zucker Rats The histological analysis of the livers of obese Zucker rats treated with the vehicle or with OLHHA confirmed the biochemistry total fat quantification results. As seen in FIG. 9, both hematoxylin-eosin staining and oil red staining showed a reduction in liver fat content in animals treated with OLHHA. Furthermore, a reduction in apoptotic activity, which is very high in fatty liver of obese rats treated with the vehicle, was seen. As can be seen in FIG. 10, OLHHA reduced the expression of both activated and total Caspase-3 (an apoptosis process mediator).

Example 11. Effect of Chronic Treatment with OLHHA on the Gene Expression of the L-FABP Protein in the Liver of Zucker Rats In addition to the reduction in the gene expression of lipogenic enzymes, as seen in FIG. 11, treatment with OLHHA increased the mRNA level of liver fatty acid-binding protein (L-FABP) involved in lipid transport and metabolism.

Example 12. Effect of Chronic Treatment with OLHHA on the Protein Levels of the Enzymes Involved in Lipid Metabolism in the Liver of Obese Zucker Rats Finally, the changes seen in the mRNA level of the lipogenic enzymes FAS and HMG-CoAR after treatment with OLHHA in obese rats were also confirmed at the protein expression level (FIG. 12).

The invention claimed is:

1. A method for relief or treatment of steatohepatitis, the method comprising administering to a subject in need thereof a composition comprising the compound N-(1-(3,4-dihydroxyphenyl)propan-2-yl)oleamide (OLHHA):

Formula (III)

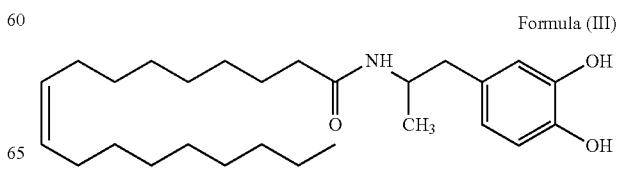

or a pharmaceutically acceptable salt, ester, tautomer, solvate or hydrate thereof.

2. The method of claim 1, wherein the steatohepatitis is non-alcoholic fatty liver disease (NAFLD).

3. The method of claim 2, where the non-alcoholic fatty liver disease (NAFLD) is non-alcoholic steatohepatitis (NASH).

4. The method of claim 1, where the composition further comprises a pharmaceutically acceptable vehicle.

5. The method of claim 1, wherein the composition is a food, nutraceutical or medical food-type composition.

6. The method of claim 1, wherein administering the composition comprising OLHHA or a pharmaceutically acceptable salt, ester, tautomer, solvate or hydrate thereof, reduces hepatic total fat in the subject.

7. The method of claim 1, wherein administering the composition comprising OLHHA or a pharmaceutically acceptable salt, ester, tautomer, solvate or hydrate thereof, reduces serum triglyceride levels in the subject and lipid accumulation in the liver of the subject.

8. The method of claim 1, wherein administering the composition comprising OLHHA or a pharmaceutically acceptable salt, ester, tautomer, solvate or hydrate thereof, reduces gene expression of lipogenic enzymes in the subject.

9. The method of claim 8, wherein the lipogenic enzymes are selected from fatty acid synthase (FAS) and 3-hydroxy-3methyl-glutaryl-CoA reductase (HMG-CoAR).

10. The method of claim 1, wherein administering the composition comprising OLHHA or a pharmaceutically acceptable salt, ester, tautomer, solvate or hydrate thereof, reduces transaminase levels in the subject.

11. The method of claim 10, wherein the transaminase is selected from aspartate transaminase (AST) and alanine transaminase (ALT).

12. The method of claim 1, wherein administering the composition comprising OLHHA or a pharmaceutically acceptable salt, ester, tautomer, solvate or hydrate thereof, reduces pro-inflammatory cytokine levels.

13. The method of claim 12, wherein the pro-inflammatory cytokine levels consist of tumor necrosis factor alpha (TNFa) in the subject.

14. The method of claim 1, wherein administering the composition comprising OLHHA or a pharmaceutically acceptable salt, ester, tautomer, solvate or hydrate thereof, reduces apoptosis in the liver of the subject.

* * * * *